United States Patent
Searle et al.

(10) Patent No.: US 10,704,944 B2
(45) Date of Patent: Jul. 7, 2020

(54) SYSTEM AND METHOD FOR CAPTURING DOSE INFORMATION

(71) Applicant: Becton, Dickinson and Company, Franklin Lakes, NJ (US)

(72) Inventors: Gary Searle, Norfolk, MA (US); Francis L Ross, III, Falls Church, VA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 284 days.

(21) Appl. No.: 14/485,749

(22) Filed: Sep. 14, 2014

(65) Prior Publication Data

US 2016/0074587 A1 Mar. 17, 2016

(51) Int. Cl.
*G01F 11/02* (2006.01)
*G01R 33/07* (2006.01)
(Continued)

(52) U.S. Cl.
CPC ....... *G01F 11/027* (2013.01); *A61M 5/14248* (2013.01); *A61M 5/16804* (2013.01);
(Continued)

(58) Field of Classification Search
CPC ............ A61M 5/14; A61M 2205/3317; A61M 5/16804; A61M 2205/3389; G01R 33/072;
(Continued)

(56) References Cited

U.S. PATENT DOCUMENTS

| | | | |
|---|---|---|---|
| 5,536,249 | A | 7/1996 | Castellano et al. |
| 5,569,212 | A | 10/1996 | Brown |

(Continued)

FOREIGN PATENT DOCUMENTS

| | | | |
|---|---|---|---|
| EP | 2060284 A1 | 5/2009 | |
| EP | 2060288 A1 | 5/2009 | |

(Continued)

OTHER PUBLICATIONS

Edward Ramsden, Hall-Effect Sensors (Second Edition), 2006, pp. xi-xiii, ISBN 9780750679343, https://doi.org/10.1016/B978-075067934-3/50001-6 (Year: 2006).*

(Continued)

*Primary Examiner* — Bradley J Osinski
(74) *Attorney, Agent, or Firm* — Dickinson Wright PLLC

(57) ABSTRACT

A system for capture of dose delivery information is provided. The system includes a medication delivery device, a dose information capture device adapted to be attached to the medication delivery device, and a target element adapted to be attached to the medication delivery device. The target element comprises a magnet or ferrous element and the target element attaches to the medication delivery device on a dose delivery mechanism of the medication delivery device. The dose information capture device includes a magnetic position sensor adapted to detect a position of the target element. As an alternative to magnetic sensing, MEMS flow sensors, and the like may also be used. Exemplary systems preferably transmit dose information in real time to remote devices for further processing.

5 Claims, 19 Drawing Sheets

(51) Int. Cl.
  *A61M 5/142* (2006.01)
  *A61M 5/168* (2006.01)
  *A61M 5/315* (2006.01)
  *A61M 5/172* (2006.01)
  *A61M 5/31* (2006.01)
  *G06F 19/00* (2018.01)
  *A61M 5/178* (2006.01)
  *B65B 3/00* (2006.01)

(52) U.S. Cl.
  CPC ........ *A61M 5/16831* (2013.01); *A61M 5/172* (2013.01); *A61M 5/31511* (2013.01); *G01R 33/072* (2013.01); *A61M 5/1782* (2013.01); *A61M 2005/3125* (2013.01); *A61M 2205/3317* (2013.01); *A61M 2205/3389* (2013.01); *A61M 2205/3576* (2013.01); *A61M 2205/50* (2013.01); *B65B 3/003* (2013.01); *G06F 19/3468* (2013.01)

(58) Field of Classification Search
  CPC ....... G01R 33/07; G11C 11/18; G01F 11/027; B65B 3/003
  See application file for complete search history.

(56) References Cited

U.S. PATENT DOCUMENTS

| | | |
|---|---|---|
| 5,593,390 A | 1/1997 | Castellano et al. |
| 5,628,309 A * | 5/1997 | Brown .............. A61M 5/31525 128/DIG. 1 |
| 5,690,618 A | 11/1997 | Smith et al. |
| 5,704,922 A | 1/1998 | Brown |
| 5,710,551 A | 1/1998 | Ridgeway |
| 5,720,733 A | 2/1998 | Brown |
| 5,728,074 A | 3/1998 | Castellano et al. |
| 5,782,814 A * | 7/1998 | Brown .................... A61M 5/00 222/23 |
| 5,792,117 A | 8/1998 | Brown |
| 5,820,602 A | 10/1998 | Kovelman et al. |
| 5,829,589 A | 11/1998 | Nguyen et al. |
| 5,873,462 A | 2/1999 | Nguyen et al. |
| 5,876,380 A | 3/1999 | Manganini et al. |
| 5,917,429 A | 6/1999 | Otis et al. |
| 5,925,021 A | 7/1999 | Castellano et al. |
| 5,931,817 A | 8/1999 | Nguyen et al. |
| 6,068,615 A | 5/2000 | Brown et al. |
| 6,084,504 A | 7/2000 | Rosche et al. |
| 6,110,148 A | 8/2000 | Brown et al. |
| 6,110,152 A | 8/2000 | Kovelman |
| 6,113,578 A | 9/2000 | Brown |
| 6,192,891 B1 | 2/2001 | Gravel et al. |
| 6,259,654 B1 | 7/2001 | De La Huerga |
| 6,270,455 B1 | 8/2001 | Brown |
| 6,277,098 B1 | 8/2001 | Klitmose et al. |
| 6,277,099 B1 | 8/2001 | Strowe et al. |
| 6,294,999 B1 | 9/2001 | Yarin et al. |
| 6,302,855 B1 | 10/2001 | Lav et al. |
| 6,346,094 B2 | 2/2002 | West et al. |
| 6,352,523 B1 | 3/2002 | Brown et al. |
| 6,379,301 B1 | 4/2002 | Worthington et al. |
| 6,380,858 B1 | 4/2002 | Yarin et al. |
| 6,482,185 B1 | 11/2002 | Hartmann |
| 6,529,446 B1 | 3/2003 | De La Huerga |
| 6,582,404 B1 | 6/2003 | Klitgaard et al. |
| 6,585,698 B1 | 7/2003 | Packman et al. |
| 6,607,508 B2 | 8/2003 | Knauer |
| 6,620,133 B1 | 9/2003 | Steck |
| 6,656,114 B1 | 12/2003 | Poulsen et al. |
| 6,830,558 B2 | 12/2004 | Flaherty et al. |
| 6,869,413 B2 | 3/2005 | Langley et al. |
| 7,008,399 B2 | 3/2006 | Larsen et al. |
| 7,060,059 B2 | 6/2006 | Keith et al. |
| 7,081,807 B2 | 7/2006 | Lai |
| 7,138,806 B2 | 11/2006 | Gafner et al. |
| 7,138,906 B2 | 11/2006 | Rosche |
| 7,195,616 B2 | 3/2007 | Diller et al. |
| 7,198,172 B2 | 4/2007 | Harvey et al. |
| 7,282,029 B1 | 10/2007 | Poulsen et al. |
| 7,295,890 B2 | 11/2007 | Jean-Pierre |
| 7,369,919 B2 | 5/2008 | Vonk et al. |
| 7,395,214 B2 | 7/2008 | Shillingburg |
| 7,405,647 B2 | 7/2008 | Rosche et al. |
| 7,424,888 B2 | 9/2008 | Harvey et al. |
| 7,454,267 B2 | 11/2008 | Bonney et al. |
| 7,466,230 B2 | 12/2008 | Bergsmann et al. |
| 7,498,563 B2 | 3/2009 | Mandro et al. |
| 7,511,480 B2 | 3/2009 | Steffen |
| 7,534,230 B2 | 5/2009 | Follman et al. |
| 7,553,234 B2 | 6/2009 | Walker et al. |
| 7,553,235 B2 | 6/2009 | Walker et al. |
| 7,591,801 B2 | 9/2009 | Brauker et al. |
| 7,695,456 B2 | 4/2010 | Langley et al. |
| 7,704,238 B2 | 4/2010 | Diller et al. |
| 7,712,288 B2 | 5/2010 | Ramasubramanian et al. |
| 7,713,229 B2 | 5/2010 | Veit et al. |
| 7,715,277 B2 | 5/2010 | De La Huerga |
| 7,731,686 B2 | 6/2010 | Edwards et al. |
| 7,740,612 B2 | 6/2010 | Hochmann |
| 7,749,186 B2 | 7/2010 | Kohlbrenner et al. |
| 7,758,545 B2 | 7/2010 | Jansen et al. |
| 7,821,404 B2 | 10/2010 | Walker et al. |
| 7,844,361 B2 | 11/2010 | Jean-Pierre |
| 7,901,383 B2 | 3/2011 | Follman et al. |
| 7,928,835 B1 | 4/2011 | Jovanov et al. |
| 7,937,829 B2 | 5/2011 | Petersen et al. |
| 7,957,983 B2 | 6/2011 | Hoffman et al. |
| 7,959,607 B2 | 6/2011 | Smit et al. |
| 7,959,609 B2 | 6/2011 | Gaydos et al. |
| 8,021,344 B2 | 9/2011 | Edwards et al. |
| 8,029,443 B2 | 10/2011 | Goodnow |
| 8,049,519 B2 | 11/2011 | Nielsen et al. |
| 8,052,655 B2 | 11/2011 | Møller et al. |
| 8,075,490 B2 | 12/2011 | Löfgren et al. |
| 8,092,224 B2 | 1/2012 | Walker et al. |
| 8,115,640 B2 | 2/2012 | Walls |
| 8,128,604 B2 | 3/2012 | Yeandel et al. |
| 8,149,096 B2 | 4/2012 | Metry et al. |
| 8,165,895 B2 | 4/2012 | Nadas et al. |
| 8,172,082 B2 | 5/2012 | Edwards et al. |
| 8,172,790 B2 | 5/2012 | Hunter et al. |
| 8,196,833 B2 | 6/2012 | McGill et al. |
| 8,197,449 B2 | 6/2012 | Nielsen et al. |
| 8,202,217 B2 | 6/2012 | Howell et al. |
| 8,206,360 B2 | 6/2012 | Edwards et al. |
| 8,221,356 B2 | 7/2012 | Enggaard et al. |
| 8,224,663 B2 | 7/2012 | Gordon |
| 8,226,610 B2 | 7/2012 | Edwards et al. |
| 8,231,573 B2 | 7/2012 | Edwards et al. |
| 8,249,894 B2 | 8/2012 | Brown |
| 8,257,310 B2 | 9/2012 | Donovan et al. |
| 8,258,962 B2 | 9/2012 | Robertson et al. |
| 8,262,394 B2 | 9/2012 | Walker et al. |
| 8,285,487 B2 | 10/2012 | Bergstrom et al. |
| 8,290,561 B2 | 10/2012 | Brauker et al. |
| 8,303,547 B2 | 11/2012 | Brown |
| 8,333,752 B2 | 12/2012 | Veit et al. |
| 8,348,840 B2 | 1/2013 | Heit et al. |
| 8,353,827 B2 | 1/2013 | Brown |
| 8,361,026 B2 | 1/2013 | Edwards et al. |
| 8,370,177 B2 | 2/2013 | Brown |
| 8,407,063 B2 | 3/2013 | Brown |
| 8,414,532 B2 | 4/2013 | Brandt et al. |
| 8,469,922 B2 | 6/2013 | Langley et al. |
| 8,489,428 B2 | 7/2013 | Brown |
| 8,491,522 B2 | 7/2013 | Takatsuka et al. |
| 8,512,279 B2 | 8/2013 | Klein |
| 8,529,520 B2 | 9/2013 | Daniel |
| 8,536,987 B2 | 9/2013 | Metry et al. |
| 8,544,645 B2 | 10/2013 | Edwards et al. |
| 8,551,039 B2 | 10/2013 | Veit et al. |
| 8,552,361 B2 | 10/2013 | Mandro et al. |
| 8,556,847 B2 | 10/2013 | Kohlbrenner et al. |
| 8,556,865 B2 | 10/2013 | Krulevitch et al. |

(56) References Cited

U.S. PATENT DOCUMENTS

| | | |
|---|---|---|
| 8,556,866 B2 | 10/2013 | Krulevitch et al. |
| 8,556,867 B2 | 10/2013 | Krulevitch et al. |
| 8,560,271 B2 | 10/2013 | Koehler et al. |
| 8,562,558 B2 | 10/2013 | Kamath et al. |
| 8,597,279 B2 | 12/2013 | Dijksman et al. |
| 8,613,719 B2 | 12/2013 | Karratt et al. |
| 8,622,241 B2 | 1/2014 | Geboers et al. |
| 8,632,509 B2 | 1/2014 | Møller et al. |
| 8,638,108 B2 | 1/2014 | Nielsen et al. |
| 2002/0093427 A1 | 7/2002 | Roth et al. |
| 2002/0104848 A1 | 8/2002 | Burrows et al. |
| 2003/0028399 A1 | 2/2003 | Davis et al. |
| 2003/0032868 A1 | 2/2003 | Graskov et al. |
| 2003/0167185 A1 | 9/2003 | Gordon et al. |
| 2004/0024361 A1 | 2/2004 | Fago et al. |
| 2004/0054263 A1 | 3/2004 | Moerman et al. |
| 2004/0054318 A1 | 3/2004 | Langley et al. |
| 2004/0158350 A1 | 8/2004 | Ostergaard et al. |
| 2004/0215492 A1 | 10/2004 | Choi |
| 2005/0038674 A1 | 2/2005 | Braig et al. |
| 2005/0055243 A1 | 3/2005 | Arndt et al. |
| 2005/0126304 A1 | 6/2005 | Sparks et al. |
| 2005/0150897 A1 | 7/2005 | Fabricius et al. |
| 2005/0171476 A1 | 8/2005 | Judson et al. |
| 2005/0197621 A1 | 9/2005 | Poulsen et al. |
| 2006/0079765 A1* | 4/2006 | Neer ............ A61M 5/007 600/432 |
| 2006/0175427 A1* | 8/2006 | Jonientz ............ A61M 5/31525 239/69 |
| 2006/0189853 A1 | 8/2006 | Brown |
| 2006/0280035 A1 | 12/2006 | Walker et al. |
| 2007/0016127 A1 | 1/2007 | Staib et al. |
| 2007/0016443 A1 | 1/2007 | Wachman et al. |
| 2007/0062250 A1* | 3/2007 | Krulevitch ........ A61M 5/16831 73/1.16 |
| 2007/0074722 A1 | 4/2007 | Giroux et al. |
| 2007/0097792 A1 | 5/2007 | Burrows et al. |
| 2007/0100222 A1 | 5/2007 | Mastrototaro et al. |
| 2007/0142777 A1 | 6/2007 | Klein |
| 2007/0184847 A1 | 8/2007 | Hansen et al. |
| 2008/0001737 A1 | 1/2008 | Metry |
| 2008/0033369 A1 | 2/2008 | Kohlbrenner et al. |
| 2008/0076973 A1 | 3/2008 | Muradia |
| 2008/0082004 A1 | 4/2008 | Banet et al. |
| 2008/0091175 A1 | 4/2008 | Frikart et al. |
| 2008/0175898 A1 | 7/2008 | Jones et al. |
| 2008/0188813 A1 | 8/2008 | Miller et al. |
| 2008/0228057 A1 | 9/2008 | Graskov et al. |
| 2008/0243088 A1* | 10/2008 | Evans ............ A61M 5/31525 604/246 |
| 2008/0277307 A1 | 11/2008 | Mazur |
| 2008/0306444 A1 | 12/2008 | Brister et al. |
| 2009/0001094 A1 | 1/2009 | Inoue et al. |
| 2009/0036753 A1 | 2/2009 | King |
| 2009/0036764 A1 | 2/2009 | Rivas et al. |
| 2009/0043253 A1 | 2/2009 | Podaima |
| 2009/0048501 A1 | 2/2009 | Goodnow |
| 2009/0076338 A1 | 3/2009 | Zdeblick et al. |
| 2009/0076458 A1 | 3/2009 | Nielsen et al. |
| 2009/0134181 A1 | 5/2009 | Wachman et al. |
| 2009/0227855 A1 | 9/2009 | Hill et al. |
| 2009/0252306 A1 | 10/2009 | Bates et al. |
| 2009/0299279 A1 | 12/2009 | Richter |
| 2010/0016700 A1 | 1/2010 | Sieh et al. |
| 2010/0106098 A1 | 4/2010 | Atterbury et al. |
| 2010/0142330 A1 | 6/2010 | Reygaert |
| 2010/0174229 A1 | 7/2010 | Hsu et al. |
| 2010/0174553 A1 | 7/2010 | Kaufman et al. |
| 2010/0219097 A1 | 9/2010 | Ramasubramanian et al. |
| 2010/0228111 A1 | 9/2010 | Friman et al. |
| 2010/0235439 A1 | 9/2010 | Goodnow |
| 2010/0268190 A1 | 10/2010 | Mielenz |
| 2010/0286612 A1 | 11/2010 | Cirillo et al. |
| 2010/0292556 A1 | 11/2010 | Golden |
| 2010/0322859 A1 | 12/2010 | Jones et al. |
| 2010/0328099 A1 | 12/2010 | Wachman et al. |
| 2011/0009821 A1 | 1/2011 | Jespersen et al. |
| 2011/0032104 A1 | 2/2011 | Cho |
| 2011/0054390 A1 | 3/2011 | Searle et al. |
| 2011/0112474 A1 | 5/2011 | Bochenko et al. |
| 2011/0118700 A1 | 5/2011 | Remde |
| 2011/0119080 A1 | 5/2011 | Hayter et al. |
| 2011/0124996 A1 | 5/2011 | Reinke et al. |
| 2011/0130720 A1 | 6/2011 | Strobl et al. |
| 2011/0152656 A1 | 6/2011 | Weinert et al. |
| 2011/0181301 A1 | 7/2011 | Nielsen et al. |
| 2011/0184281 A1 | 7/2011 | Fago et al. |
| 2011/0184343 A1 | 7/2011 | Veit et al. |
| 2011/0184748 A1 | 7/2011 | Fierro et al. |
| 2011/0190701 A1 | 8/2011 | Remde et al. |
| 2011/0257602 A1 | 10/2011 | Watanabe et al. |
| 2011/0264033 A1 | 10/2011 | Jensen et al. |
| 2011/0264035 A1 | 10/2011 | Yodfat et al. |
| 2011/0270188 A1* | 11/2011 | Caffey ............ A61M 5/14526 604/151 |
| 2011/0270214 A1 | 11/2011 | Jørgensen et al. |
| 2011/0295215 A1 | 12/2011 | Nielsen et al. |
| 2011/0313395 A1 | 12/2011 | Krulevitch et al. |
| 2012/0010600 A1 | 1/2012 | Wilinska et al. |
| 2012/0022458 A1 | 1/2012 | Oh |
| 2012/0035542 A1 | 2/2012 | Pongprairochana |
| 2012/0041417 A1 | 2/2012 | Searle et al. |
| 2012/0053527 A1 | 3/2012 | Cirillo et al. |
| 2012/0065588 A1 | 3/2012 | Cirillo et al. |
| 2012/0071819 A1 | 3/2012 | Brüggemann et al. |
| 2012/0072236 A1 | 3/2012 | Atkin |
| 2012/0084094 A1 | 4/2012 | Brown |
| 2012/0095313 A1 | 4/2012 | Reinke et al. |
| 2012/0143142 A1 | 6/2012 | Klein |
| 2012/0158424 A1 | 6/2012 | Knudsen et al. |
| 2012/0197534 A1 | 8/2012 | Kavusi et al. |
| 2012/0215162 A1 | 8/2012 | Nielsen et al. |
| 2012/0222468 A1 | 9/2012 | Nelson et al. |
| 2012/0226446 A1 | 9/2012 | Nelson et al. |
| 2012/0226447 A1 | 9/2012 | Nelson et al. |
| 2012/0238851 A1 | 9/2012 | Kamen et al. |
| 2012/0245716 A1 | 9/2012 | Srinivasan et al. |
| 2012/0268741 A1 | 10/2012 | Pommereau et al. |
| 2012/0277543 A1 | 11/2012 | Homchowdhury et al. |
| 2012/0289803 A1 | 11/2012 | Weinert et al. |
| 2012/0295240 A1 | 11/2012 | Walker et al. |
| 2012/0296276 A1 | 11/2012 | Nicholls et al. |
| 2012/0296311 A1 | 11/2012 | Brauker et al. |
| 2012/0302947 A1 | 11/2012 | Canton |
| 2012/0316414 A1 | 12/2012 | Greene |
| 2012/0323184 A1 | 12/2012 | Oh |
| 2012/0323590 A1 | 12/2012 | Udani |
| 2012/0323796 A1 | 12/2012 | Udani |
| 2012/0323805 A1 | 12/2012 | Udani |
| 2012/0330228 A1 | 12/2012 | Day et al. |
| 2013/0023822 A1 | 1/2013 | Edwards et al. |
| 2013/0023825 A1 | 1/2013 | Edwards et al. |
| 2013/0072897 A1 | 3/2013 | Day et al. |
| 2013/0073312 A1 | 3/2013 | Thompson et al. |
| 2013/0079708 A1 | 3/2013 | Wimpenny et al. |
| 2013/0079727 A1 | 3/2013 | Schildt et al. |
| 2013/0103424 A1 | 4/2013 | Brown |
| 2013/0116818 A1 | 5/2013 | Hamilton |
| 2013/0123685 A1 | 5/2013 | Jespersen et al. |
| 2013/0123719 A1 | 5/2013 | Mao et al. |
| 2013/0124224 A1 | 5/2013 | Srinivasan et al. |
| 2013/0125158 A1 | 5/2013 | Brown |
| 2013/0173268 A1 | 7/2013 | Weng et al. |
| 2013/0179189 A1 | 7/2013 | Brown |
| 2013/0184649 A1 | 7/2013 | Edwards et al. |
| 2013/0190692 A1 | 7/2013 | Edwards et al. |
| 2013/0197445 A1 | 8/2013 | Schabbach et al. |
| 2013/0211212 A1 | 8/2013 | Stumber |
| 2013/0221097 A1 | 8/2013 | Day et al. |
| 2013/0222135 A1 | 8/2013 | Stein et al. |
| 2013/0226137 A1 | 8/2013 | Brown |
| 2013/0226139 A1 | 8/2013 | Day et al. |
| 2013/0226339 A1 | 8/2013 | Ervin |
| 2013/0245545 A1 | 9/2013 | Arnold et al. |

(56) References Cited

U.S. PATENT DOCUMENTS

| | | |
|---|---|---|
| 2013/0253699 A1 | 9/2013 | Reimer |
| 2013/0256331 A1 | 10/2013 | Giraud et al. |
| 2013/0280687 A1 | 10/2013 | Edwards et al. |
| 2013/0310756 A1 | 11/2013 | Whalley |
| 2013/0319902 A1 | 12/2013 | Tufi |
| 2013/0321426 A1 | 12/2013 | Kamath et al. |
| 2013/0323699 A1 | 12/2013 | Edwards et al. |
| 2013/0324920 A1 | 12/2013 | Kohli et al. |
| 2013/0325501 A1 | 12/2013 | Walker et al. |
| 2013/0336555 A1 | 12/2013 | Baek et al. |
| 2013/0345640 A1 | 12/2013 | Klein |
| 2013/0345641 A1 | 12/2013 | Cerman et al. |
| 2014/0005596 A1 | 1/2014 | Schuster |
| 2014/0005603 A1 | 1/2014 | Holtwick et al. |
| 2014/0018730 A1 | 1/2014 | Müller-Pathle |
| 2014/0018733 A1 | 1/2014 | Sjølund et al. |
| 2014/0276583 A1 | 9/2014 | Chen et al. |

FOREIGN PATENT DOCUMENTS

| | | |
|---|---|---|
| EP | 2327431 A1 | 6/2011 |
| EP | 2369516 A2 | 9/2011 |
| EP | 2537546 A1 | 12/2012 |
| JP | 2006099301 A | 4/2006 |
| WO | WO1995009386 A1 | 4/1995 |
| WO | WO2001072260 A1 | 10/2001 |
| WO | WO2002041825 A2 | 5/2002 |
| WO | WO3047426 A1 | 6/2003 |
| WO | 03/060436 A2 | 7/2003 |
| WO | WO2003075823 A1 | 9/2003 |
| WO | WO2006035278 A1 | 4/2006 |
| WO | WO2006125692 A1 | 11/2006 |
| WO | WO2007043858 A2 | 4/2007 |
| WO | WO2007060588 A1 | 5/2007 |
| WO | WO2007096898 A2 | 8/2007 |
| WO | WO2007104531 A1 | 9/2007 |
| WO | WO2008120156 A2 | 10/2008 |
| WO | WO-2009039203 A2 | 3/2009 |
| WO | WO2009062673 A1 | 5/2009 |
| WO | WO2009062675 A1 | 5/2009 |
| WO | WO2009141650 A2 | 11/2009 |
| WO | WO2009156832 A1 | 12/2009 |
| WO | WO2010035056 A1 | 4/2010 |
| WO | WO2010096061 A1 | 8/2010 |
| WO | WO2011023628 A1 | 3/2011 |
| WO | WO2011054000 A1 | 5/2011 |
| WO | WO2011064299 A1 | 6/2011 |
| WO | WO2012046199 A1 | 4/2012 |
| WO | WO2012067840 A1 | 5/2012 |
| WO | WO2012085031 A1 | 6/2012 |
| WO | WO2012110700 A1 | 8/2012 |
| WO | WO2012110701 A1 | 8/2012 |
| WO | WO2012129120 A1 | 9/2012 |
| WO | WO2012130992 A1 | 10/2012 |
| WO | WO2012140097 A2 | 10/2012 |
| WO | WO2012160156 A2 | 11/2012 |
| WO | WO2012160157 A1 | 11/2012 |
| WO | WO2012160159 A1 | 11/2012 |
| WO | WO2012160166 A1 | 11/2012 |
| WO | WO2012175503 A1 | 12/2012 |
| WO | WO2013004843 A1 | 1/2013 |
| WO | WO2013004844 A1 | 1/2013 |
| WO | WO2013010884 A1 | 1/2013 |
| WO | WO2013010889 A1 | 1/2013 |
| WO | WO2013034716 A1 | 3/2013 |
| WO | WO2013040494 A1 | 3/2013 |
| WO | WO2013045506 A1 | 4/2013 |
| WO | WO2013050535 A2 | 4/2013 |
| WO | WO2013053695 A1 | 4/2013 |
| WO | WO2013072443 A1 | 5/2013 |
| WO | WO2013076026 A1 | 5/2013 |
| WO | WO2013093059 A1 | 6/2013 |
| WO | WO2013101818 A1 | 7/2013 |
| WO | WO2013120775 A1 | 8/2013 |
| WO | WO2013120777 A1 | 8/2013 |
| WO | WO2013120778 A1 | 8/2013 |
| WO | WO2013150109 A1 | 10/2013 |
| WO | WO2013156510 A1 | 10/2013 |

OTHER PUBLICATIONS

Hall Effect, http://hyperphysics.phy-astr.gsu.edu/hbase/magnetic/Hall.html (Year: 2019).*

An Electronic Pillbox for Continuous Monitoring of Medication Adherence, Hayes et al., Conf Proc IEEE Eng Med Biol Soc. 2006;1:6400-3.

Functionality and acceptability of a new electronic insulin injection pen with a memory feature, Venekamp et al., Curr Med Res Opin. Feb. 2006;22(2):315-25.

Auto-Injectors: Technology Advances and Market Trends, Barrow-Williams et al., Innovations in Pharmaceutical Technology.

Electronic pillboxes (MEMS) to assess the relationship between medication adherence and blood pressure control in primary care, Zeller et al., Scandinavian Journal of Primary Health Care, 2007; 25: 202 207.

Monitoring Medicine Intake in the Networked Home: The iCabiNET Solution, Martin López-Nores et al., Pervasive Computing Technologies for Healthcare, 2008. PervasiveHealth 2008. Second International.

An Asymmetric RF tagging IC for Ingestible Medication Compliance Capsules, Hong Yu et al., 2009 IEEE Radio Frequency Integrated Circuits Symposium.

Novopen Echo® for the Delivery of Insulin: a Comparison of Usability, Functionality and Preference among Pediatric Subjects, Their Parents, and Health Care Professionals, Olsen et al., J Diabetes Sci Technol. Nov. 1, 2010;4(6):1468-75.

Novel Ingestible Capsule Antenna Designs for Medical Monitoring and Diagnostics, Harish Rajagopalan et al., Antennas and Propagation (EuCAP), 2010 Proceedings of the Fourth European Conference on.

Lessons Learned during the Development of HumaPen® Memoir™, an Insulin Pen with a Memory Feature, Breslin et al., J Diabetes Sci Technol. May 1, 2010;4(3):540-6.

Insulin Pen Use for Type 2 Diabetes—A Clinical Perspective, Bailey et al., Diabetes Technol Ther. Jun. 2010;12 Suppl 1:S86-90. doi: 10.1089/dia.2010.0032.

Dynamically Programmable Electronic Pill Dispenser System, Boquete et al., J Med Syst. Jun. 2010;34(3):357-66.

PositiveID Corporation Files Patent for Innovative Diabetes Management Tool, an Insulin Data Tracking and Communication Device, www.globenewswire.com.

Analysis of the NovoPen® Echo for the Delivery of Insulin: A Comparison of Usability, Functionality, and Preference among Pediatric Subjects, Their Parents, and Health Care Professionals, Reynholds et al., J Diabetes Sci Technol. Nov. 1, 2010;4(6):1476-8.

Pendiq Intelligent Insulin Pen, www.pendiq.com.

Novo Nordisk's new insulin pen for children receives 2010 Good Design Award, http://www.news-medical.net/news/20110119/Novo-Nordisks-new-insulin-pen-for-children-receives-2010-GOOD-DESIGN-Award.aspx.

Treatment adherence with the easypod™ growth hormone electronic auto-injector and patient acceptance: survey results from 824 children and their parents, Bozzola M, Colle M, Halldin-Stenlid M, Larroque S, Zignani M; easypod™ survey study group., BMC Endocr Disord. Feb. 4, 2011;11:4. doi: 10.1186/1472-6823-11-4.

Dose accuracy and durability of a durable insulin pen before and after simulated lifetime use, Kristensen CM, Lilleøre SK., Curr Med Res Opin. Oct. 2011;27(10):1877-83. doi: 10.1185/03007995.2011. 609885. Epub Aug. 30, 2011.

A Smart Medication System Using Wireless Sensor Network Technologies, W.-W. Chang et al., Sensors and Actuators: A Physical (2010), doi:10.1016/j.sna.2011.03.022.

Automated NFC Enabled Rural Healthcare for Reliable Patient Record Maintainance, Sethia et al., Stud Health Technol Inform. 2012;182:104-13.

Objective adherence measurement with a smart blister—A feasibility study in primary care, Hein AW van Onzenoort et al., Treatment

(56) References Cited

OTHER PUBLICATIONS adherence in hypertension methodological aspects and new strategies Accepted by American Journal of Health-System Pharmacy, Ch. 7, 111-123.
Odd Couplings: Drug firms engage in Nontraditional Research Partnerships in a bid to get closer to the patient, Mullin, Rick, www.CEN-ONLINE.org.
A Smart Diagnostic Capsule with a Novel Antenna and Nano-Biosensors, H. Rajagopalan et al., 6th European Conference on Antennas and Propagation (EUCAP).
Feasibility of mHealth and Near Field Communication Technology based Medication Adherence Monitoring, Morak J et al., Conf Proc IEEE Eng Med Biol Soc. 2012;2012:272-5. doi: 10.1109/EMBC.2012.6345922.
Safety and patient perception of an insulin pen with simple memory function for children and adolescents with type 1 diabetes—the Remind study, Adolfsson P, et al., Curr Med Res Opin. Sep. 2012;28(9):1455-63. Epub Jul. 27, 2012.
SMS reminders improve adherence to oral medication in type 2 diabetes patients who are real time electronically monitored, Vervloet M, v et al., Int J Med Inform. Sep. 2012;81(9):594-604. doi: 10.1016/j.ijmedinf.2012.05.005. Epub May 30, 2012.
Mobile Phone-Based Pattern Recognition and Data Analysis for Patients with Type 1 Diabetes, Skrøvseth et al., Diabetes Technol Ther. Dec. 2012;14(12):1098-104. doi: 10.1089/dia.2012.0160. Epub Oct. 4, 2012.
Smart medication management system and multiple interventions for medication adherence, Upkar Varshney, Decision Support Systems 55 (2013) 538-551.
An Analysis of "No Effect of Insulin Pen with Memory Function on Glycemic Control in a Patient Cohort with Poorly Controlled Type 1 Diabetes: A Randomized Open-Label Study", Ampudia-Blasco FJ., J Diabetes Sci Technol. Nov. 1, 2012;6(6):1398-400.
Miniature wireless sensors presage smart phone medicine, Eisenstein M., Nat Biotechnol. Nov. 2012;30(11):1013-4. doi: 10.1038/nbt1112-1013.
Mobile Phone Tools with Ambient Intelligence for the Management of Life-Threatening Allergies, Hernandez-Munoz, L.U., Woolley, S.I., T. Bosse et al. (eds.), Human Aspects in Ambient Intelligence, Atlantis Ambient and Pervasive Intelligence 8, DOI: 10.2991/978-94-6239-018-8_10.
Insulin Pens and New Ways of Insulin Delivery, Heinemann L., Diabetes Technol Ther. Feb. 2013;15 Suppl 1:S48-59. doi: 10.1089/dia.2013.1506.
Feasibility of an Ingestible Sensor-Based System for Monitoring Adherence to Tuberculosis Therapy, Belknap et al., PLoS One. 2013;8(1):e53373. doi: 10.1371/journal.pone.0053373. Epub Jan. 7, 2013.
A Smartphone-based Medication Self-management System with Realtime Medication Monitoring, Hayakawa et al., Appl Clin Inform. Jan. 30, 2013;4(1):37-52. doi: 10.4338/ACI-2012-10-RA-0045. Print 2013.
An Automatic Medication Self-Management and Monitoring System for Independently Living Patients, McCall C et al., Med Eng Phys. Apr. 2013;35(4):505-14. doi: 10.1016/j.medengphy.2012.06.018. Epub Jul. 22, 2012.
Evaluation of preference for a novel durable insulin pen with memory function among patients with diabetes and health care professionals, Klausmann et al., Patient Prefer Adherence. Apr. 5, 2013;7:285-92. doi: 10.2147/PPA.S41929. Print 2013.
Emperra® GmbH E-Health Technologies completes a €2.6 million financing round led by the Peppermint Charité Biomedical Fund and Goodvent with existing investors BC Brandenburg Capital and MBG participating, Mertens et al., www.emperra.com.
New improved Insulcheck launched, www.insulcheck.com.
A Syringe Injection Rate Detector Employing a Dual Hall-Effect Sensor Configuration, Mukherjee et al., Conf Proc IEEE Eng Med Biol Soc. 2013;2013:4734-7. doi: 10.1109/EMBC.2013.6610605.
Design and Evaluation of a Multimodal mHealth based Medication Management System for Patient Self Administration, Schreier et al., Conf Proc IEEE Eng Med Biol Soc. 2013;2013:7270-3. doi: 10.1109/EMBC.2013.6611236.
Medication Adherence Assessment: High Accuracy of the New Ingestible Sensor System in Kidney Transplants, Eisenberger et al., Transplantation. Aug. 15, 2013;96(3):245-50. doi: 10.1097/TP.0b013e3182967571.
Novo Nordisk receives U.S. FDA clearance for the insulin injection device NovoPen Echo® First insulin injection device to combine half-unit dosing with a memory function to help patients better manage their diabetes, Novo Nordisk receives U.S. FDA clearance for the insulin injection device NovoPen Echo®—Aug. 21, 2013.
Mobile health (mHealth) based medication adherence measurement—a pilot trial using electronic blisters in diabetes patients, Brath et al., Br J Clin Pharmacol. Sep. 2013;76 Suppl 1:47-55. doi: 10.1111/bcp.12184.
Smart NFC-sensors for healthcare applications and further development trends, Cecil et al., Elektrotechnik & Informationstechnik (2013) 130/7: 191-200. DOI 10.1007/s00502-013-0156-y.
Novo Nordisk Announces U.S. Launch of New Insulin Injection Device NovoPen Echo® Pen is first insulin injection device combining half-unit dosing and memory function, Novo Nordisk Announces U.S. Launch of New Insulin Injection Device NovoPen Echo®—Jan. 21, 2014.
A Pocketsized Smart Phone Accessory Medical Auto-Injector, Pribitkin, Edmund, Thomas Jefferson University.
Pendiq Intelligent Insulin Pen: User Manual, www.pendiq.com.
The Smart Insulin Pen, Diabetesnet.com.
The highly innovative tele-diabetological closed loop system for optimized care of insulin-dependent Diabetes mellitus Types 1 and 2, N/A, www.emperra.com.
Piccolo Injector, http://verus.ie/device-design/.
Autoinjector With Wireless Communication, Kajsa Bobjer, http://www.zenitdesign.se/#!/zenit_projects_32.
Position and Level Sensing Using Hall Effect Sensing Technology, Application Information, Gary Pepka, Allegro™ MicroSystems, LLC.
Applications of Magnetic Position Sensors, Application Note, Honeywell Sensor Products.
Hall-Effect IC Applications Guide, Application Note, Allegro Microsystems, Inc.
Technical Advances in Hall-Effect Sensing, Technical Paper, Joe Gilbert, Allegro Microsystems, Inc.

\* cited by examiner

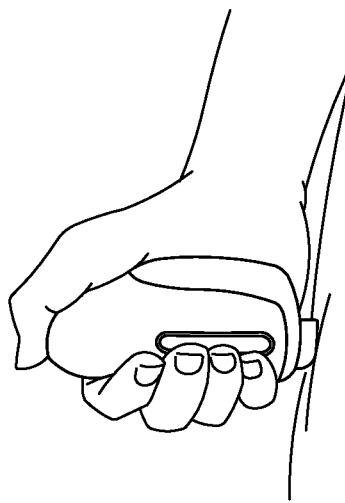
FIG. 8
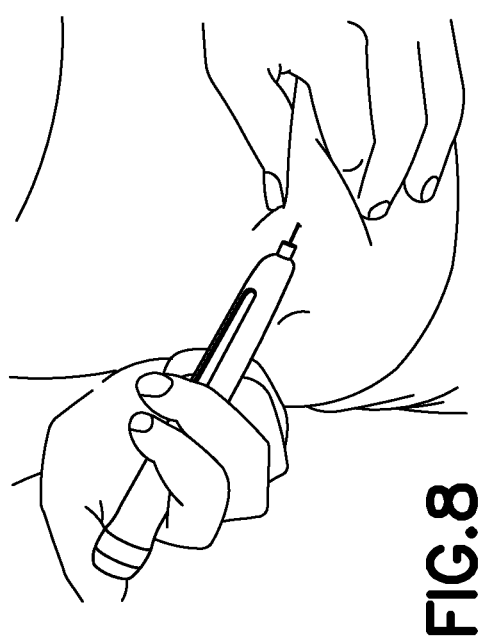
FIG. 9
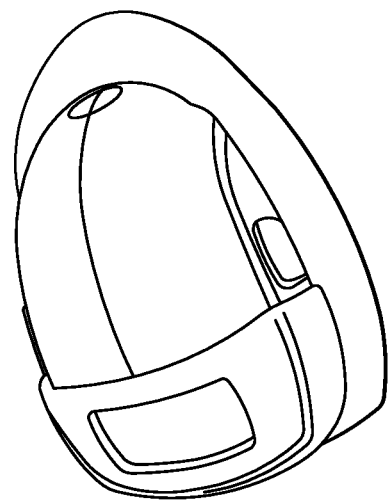
FIG. 10
FIG. 11

SYSTEM AND METHOD FOR CAPTURING DOSE INFORMATION

FIELD OF THE INVENTION

The present invention relates to systems and methods for capturing the volume of medication delivered by a syringe or other medication delivery device. In particular, the present invention relates to systems and methods for utilizing magnetic position sensing such as Hall-effect sensing and magnetoresistive (MR) sensing, Micro Electro Mechanical Systems (MEMS) flow sensing, and the like in connection with various medication delivery devices and components to capture medication dose delivery information.

BACKGROUND OF THE INVENTION

Diabetes is a group of diseases marked by high levels of blood glucose resulting from defects in insulin production, insulin action, or both. There are 25.8 million people in the United States, or 8.3% of the population, who have diabetes. The total prevalence of diabetes has increased 13.5% since the 2005-2007 time period. Diabetes can lead to serious complications and premature death, but there are well-known products available for people with diabetes to help control the disease and lower the risk of complications. Chronic hyperglycemia leads to serious sometimes irreversible complications including renal failure, peripheral neuropathy, retinopathy, and vascular system complications.

Treatment options for people with diabetes include specialized diets, oral medications and/or insulin therapy. The primary goal for diabetes treatment is to control the patient's blood glucose (sugar) level in order to increase the chances of a complication-free life.

Idealized diabetes therapy would include continuous monitoring of blood glucose levels, data capture for insulin dosing, dietary intake, such as carbohydrate estimation, activity tracking, stress levels, and other factors. By continuously monitoring, healthcare professionals can maximize the effectiveness of the treatment regimen for each patient. Unfortunately, conventional diabetes treatments, including multiple daily injections (MDI), insulin pens, patch pumps and insulin pumps, do not adequately record information on medication doses delivered to the patient to provide feedback to the doctor. Accordingly, the conventional feedback loop between doctors and patients is less frequent, and based mainly on qualitative assessments between the doctor and patient. Accordingly, there is a need to enhance medication delivery devices and methods to add informatics such as dose delivery capture, to provide enhanced feedback to healthcare professionals to improve diabetes therapy.

In order to properly diagnose and treat diabetes mellitus (DM) the patient and/or Health Care Provider (HCP) needs to evaluate the short-term, daily records for (1) insulin dosing, (2) oral medications, (3) Blood Glucose Measurement (BGM), and (4) carbohydrate intake. These data are obtained from different sources, such as the setting on an insulin pen, the episodic reading from a BGM meter, and the estimate of carbohydrates in a meal all determined and transposed by the patient into a logbook or diary. This method of recording data is extremely tedious and prone to errors and omissions. Even in the best case scenario, when the historical records are complete, the insight that can be obtained is limited without transposing the hand written data to software that can reconfigure the data to evaluate trends and support therapeutic modifications. As a result the majority of patients do not properly maintain their logbook, which reduces the ability of the patient and the doctor to properly diagnose the disease, which can ultimately result in poor adherence to therapy and poor glycemic control. Accordingly, a system is required to automatically capture, store, transfer, and enable optimal assessment of all the data necessary for the proper diagnosis and treatment of Diabetes Mellitus.

U.S. Pat. No. 8,613,719 describes a monitor that can be attached to the patch pen, which can sense and wirelessly transmit the time of each delivery event. A flag, such as a magnet, is placed on the movable linkage within the patch pen, and a sensor within the monitor attachment detects the proximity of the magnet at the end of the linkage travel, that is, at the end of the delivery cycle.

SUMMARY OF THE INVENTION

The above described disadvantages are overcome or minimized and the above and other advantages are realized by embodiments of the present invention. Exemplary embodiments of the present invention provide a device for capturing delivered dose information. The device includes a medication delivery device, a dose information capture device adapted to be attached to the medication delivery device, and a sensor element adapted to be attached to the medication delivery device. The sensor element comprises at least one of either a magnet, preferably a permanent magnet, although a non-permanent magnet could be used, and at least one a ferrous element, and attaches to the medication delivery device on a dose delivery mechanism of the medication delivery device. The dose information capture device includes a magnetic position sensor adapted to detect a position of the sensor element.

Accordingly, embodiments of the present invention provide a device that senses a delivered dose by magnetic position sensing. Magnetic position sensing is accomplished by Hall-effect sensors, magnetoresistive sensors, or any other suitable device. Various embodiments may sense linear translation, rotational movement, flow, or medication level within an insulin vial or reservoir. Magnetic position sensing determines linear or rotational movement of the mechanical linkage or mechanization that correlates with the dose to be delivered in an insulin pen or other drug delivery device, as will be described herein. In other embodiments magnetic position sensing is utilized to determine the level of fluid in a vessel, such as by linear translation or change in position of a magnet floating on a top surface of insulin. Flow sensing, particularly MEMS flow sensors, include coriolis, capacitance, and thermal Time of Flight (ToF) sensors used to determine the volume of drug delivered from a pen, syringe or other drug delivery device. Capacitance sensing is preferably used to measure and determine the level of liquid, such as insulin, in a vessel such as an insulin vial.

BRIEF DESCRIPTION OF THE DRAWINGS

The above and other exemplary features and advantages of certain exemplary embodiments of the present invention will become more apparent from the following description of certain exemplary embodiments thereof when taken in conjunction with the accompanying drawings, in which:

FIG. 8 illustrates a fixed dose pen

FIG. 9 is another illustration of either an adjustable or fixed dose pen.

FIGS. 10 and 11 illustrate embodiments of informatically enabled mechanical patch pens according to exemplary embodiments of the invention;

Throughout the figures, like reference numbers will be understood to refer to like elements, features and structures.

DETAILED DESCRIPTION OF EXEMPLARY EMBODIMENTS

Figure 1:
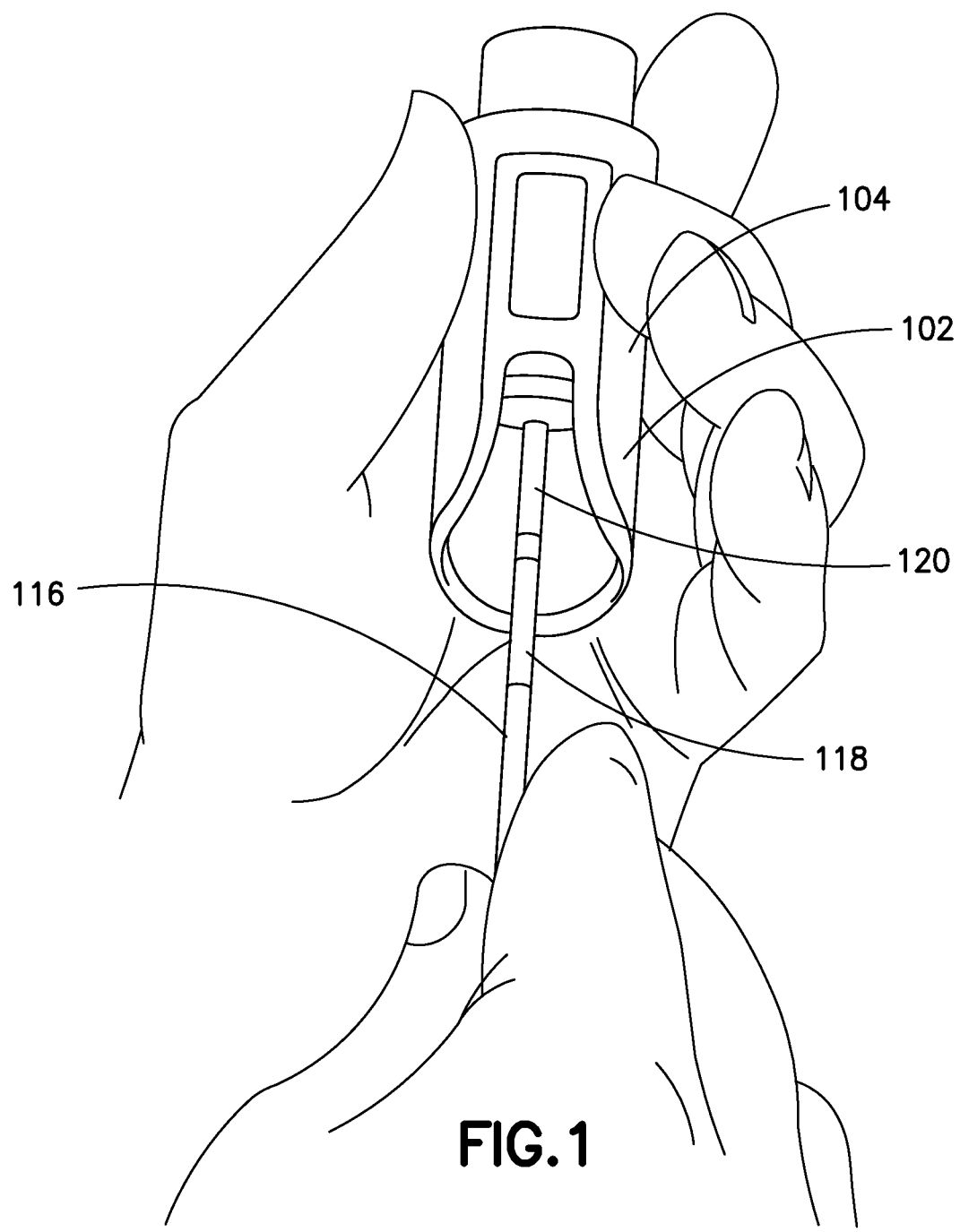
FIG. 1 illustrates an informatically enabled vial sleeve according to an exemplary embodiment of the present invention.

In the example provided below, insulin delivery is described. However, it should be understood that insulin delivery is merely exemplary, and any medicament delivery is contemplated to be within the scope of the invention. Informatics is defined herein as an interdisciplinary field primarily concerned with the analysis, collection, classification, manipulation, storage, retrieval, movement, and dissemination of information.

Exemplary embodiments of the present invention capture the amount or volume of medicament being delivered by either a syringe, insulin pen, or other drug delivery device. Several primary fields of technology, magnetic position sensing including Hall-effect sensing, magnetoresistive (MR) sensing, including anisotropic MR, MEMS flow sensing including thermal time of flight (ToF) sensing, micro-Coriolis and capacitive pressure sensing, are applied to various devices and device components to enable dose capture. MEMS capacitive pressure sensing uses Bernoulli's principle and/or the empirical Darcy-Weisbach equation are utilized to detect a change in pressure by changing the diameter of the conduit in the flow sensing element, and the pressure is measured using two capacitive MEMS pressure sensors located respectively in sections of conduit having different diameters. In the exemplary embodiments described herein, it should be understood that any type of MEMS flow sensing may be utilized in place of magnetic position sensing. It should be understood that embodiments of the present invention are not limited to Hall-effect sensing and MEMS flow sensing, but rather any suitable sensing technology is within the scope of the present invention.

Conventional Hall sensors are sensitive only to magnetic fields that are perpendicular to the chip surface, that is, one dimensional or 1D. 3D Hall sensors advantageously also respond to magnetic fields parallel to the chip surface. The sensor chip has a separate sensor for each of the three magnetic axes, and converts the magnetic field data into absolute position information using a simple two pole magnet as the magnetic field source. For a linear sensing application, the 3D Hall sensor would be used in 2D mode. One advantage of this system for linear sensing is that it allows for larger separation between magnet source and sensor than standard 1D Hall sensors.

A basic Anisotropic Magnetoresistive (AMR) sensor uses a single saturated-mode Wheatstone bridge, typically made from Permalloy (Ni—Fe alloy), that creates an output voltage with respect to the direction of the magnetic flux passing over the sensor surface. Thus it operates in saturation mode to avoid interference from stray magnetic fields and the magnetic field that it senses is across the face of the chip, contrasting with the perpendicular field of a Hall sensor. The AMR sensor creates an analog output voltage that varies with the direction of the magnetic flux passing over the chip surface. The minimum field required to put the AMR sensor into saturation mode is typically 50-80 gauss. A single element AMR sensor has a ±45° range of operation where voltage-to-angle output is linear.

Embodiments of the present invention preferably meet the following functional capabilities. First, embodiments of the present invention preferably electronically capture the amount of pharmaceutical injected and the time of the injection event. Second, they preferably provide a means of associating the captured injection event data with the type of pharmaceutical injected. Drug identification technology may be incorporated into embodiments of the present invention, and are described in U.S. Published Application Nos. 2012/0222468, 2012/0226447, and 2012/0226446, the entire contents of each of which are hereby incorporated by reference in their entirety. Third, they are preferably compatible with existing, commonly prescribed diabetes pharmaceutical pens and other devices utilized for MDI or infusion therapy. Fourth, they transmit captured data in a common digital format compatible with smart phones or similar devices to be utilized in patient software such as a patient meaning engine. A patient meaning engine receives data, including patient blood glucose levels, calorie intake, exercise, medication doses, and other relevant data. One function of the engine is to track trends in the data and provide feedback to a user to enhance the effectiveness of patient self-care through improved understanding of the patient's disease and therapy in the patient's daily life. The meaning engine provides feedback to the patient to promote self-therapy and enables improved decision making during dosing events, e.g. prandial dosing. This feedback and the additional insight afforded by the meaning engine provide sufficient value to the patient during dosing events to influence behavioral modification. The meaning engine can also provide information or alerts to healthcare providers so that deviations from healthy trends are identified and proactively acted upon. The use of a meaning engine as defined herein promotes efficient use of physician time and eliminates or reduces poor medical treatment regimens that rely on fail-first as opposed to identifying the shortest path to a cost effective outcome. Fifth, they preferably transmit captured data to the patient meaning engine within one minute of sensing the delivered dose. Sixth, they capture data from all prescribed forms of T1 and T2 insulin and oral dose regimens. Seventh, their accuracy preferably satisfies injection standard ISO 11608. One example of utilizing the meaning engine would be titrating a new drug for a patient. Patients using a new drug, such as slow acting insulin, for the first time, by adjusting the dose each day based on analyzing insulin doses delivered and blood glucose readings over a period of time. The adjustments and data could be sent to the patient's doctor to close the loop between the doctor and patient daily while saving time for the doctor and expediting the titration process for the patient. Of course insulin is used herein as an example, and any suitable drug could similarly be titrated by monitoring relevant factors such as medicine doses and blood glucose levels or the like.

Embodiments of the present invention further preferably meet the following additional criteria. They can be carried with the patient and used anytime, anywhere. They preferably do not increase the number of items a diabetes patient normally carries. They are compatible with other elements in an informatics enabled outcome (IEO) system, such as Blood Glucose Monitors (BGM) and oral medicine adherence devices; that is, data transfer between devices in the system utilize a common communication platform.

Embodiments of the present invention are preferably easy for the patient to use; that is, the device or system functionality preferably does not require a high level of user expertise or significant training Embodiments of the present invention improve patient safety, and preferably do not compromise patient safety in any way.

Exemplary embodiments of the present invention informatically enable medicament delivery devices to affirmatively capture dose delivery information. The following devices and device components typically associated with dose delivery are appropriate for informatics enablement. A vial attachment can sense movement of a syringe plunger. A pen cap can sense movement of the plunger in an insulin pen by magnetic sensing means. A magnetic sensor is preferably incorporated into a disposable insulin pen to determine plunger position. A sleeve with an integral flow sensor can be placed between an insulin pen and a pen needle. A cartridge for a reusable pen can include a sensor to determine plunger position in the cartridge. A cartridge filler can be utilized to attach a sensing element to a cartridge. A mechanism attached to the end of an insulin pen that exchanges a cannula into and from a reusable cannula hub can be provided with a flow sensor. A pen case may be provided with a magnetic position sensor to determine the position of a plunger within an insulin pen when returned to its pen case. A patch pump configured to deliver a preset number of insulin units per activation (button press) can be configured with a sensor to sense button presses. An injection patch, similar to the Insuline "Insupad" can be modified to channel the flow from different injections through a flow sensor. An injection port, similar to the device provided by Patton Medical, can also be modified in the same manner. An insulin vial or fluid reservoir can be modified to incorporate an internal floating magnet and an external sleeve with integrated magnetic sensors. Any all-in-one type device can be provided with appropriate sensors as described herein to capture dose information. As used herein, an "All-In-One" device should be understood to be a combination device, such as a device which includes for example a BGM and a method to deliver insulin dosing or a BGM and a bolus calculator. An attachment for a syringe in which at least one sensor element is connected to the syringe plunger and at least one sensor is attached to the syringe barrel.

A first embodiment of the invention is shown in FIG. 1 which shows an attachment 102 for an insulin vial and a modified insulin syringe. A reusable attachment 102 engages with an insulin vial, and preferably remains attached until the insulin is exhausted. The vial attachment 102 includes at least one linear Hall-effect sensor 104 with an analog output, a flexible Printed Circuit Board Assembly (PCBA) 106, a battery 108, a power management system 110, a Bluetooth Low Energy (BLE) wireless transceiver 112, and a Real Time Clock (RTC) 114. During the manufacturing process for the syringe 116, an RFID chip 118 is placed into the syringe 116, and a permanent magnet 120 is over-molded into the stopper or plunger. In an alternate embodiment a ferrous target, such as a steel disc or slug, is used rather than a magnet to further reduce the cost of the disposable significantly.

When a ferrous target is utilized, the Hall-effect sensor 104 is preferably back biased by integrating a magnet with the Hall sensor 104, so that a ferrous object in range will be sensed by the Hall sensor 104.

The vial attachment 102 reads the RFID chip in the syringe 116 to determine the inner diameter (ID) of the syringe barrel. The Hall-effect sensor 104 measures the linear movement of the plunger, and the dose is calculated from the ID and the plunger travel. The dose amount is time stamped and wirelessly transferred to a smart phone and/or to the "cloud" or internet. Alternately, a phone application (APP) for a Smart phone is provided in which the phone camera captures an image of the syringe just prior to injection. The syringe diameter would be recognized either by a bar code, a QR code, or the like printed on the outside of the syringe barrel, or a comparative measurement, or other optical methods that are part of a Smart phone, and the distance between the plunger and the nozzle, just prior to injection, could be determined by the same method. Similarly to the previous embodiment, these two values are then used to calculate the dose. The numerous features described herein can also be combined to provide additional embodiments, e.g. the Smart phone APP could replace the need for the RFID chip, in combination with a vial attachment that measures the movement of the plunger by sensing the position of the embedded magnet.

Figure 2A:
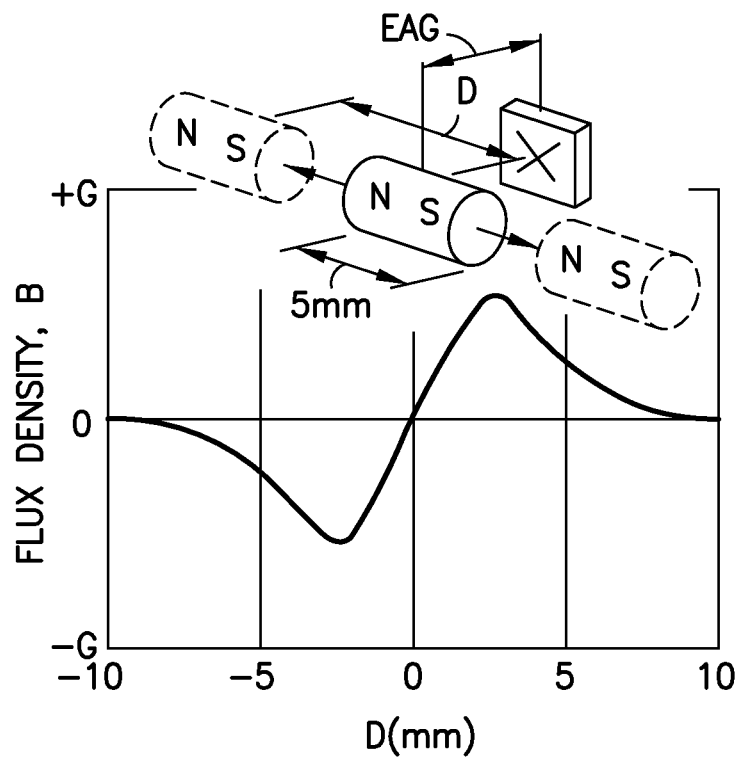
FIG. 2A illustrates flux density over distance in a Hall-effect sensor and magnet arrangement utilized with an exemplary embodiment of the present invention.
Figure 2B:
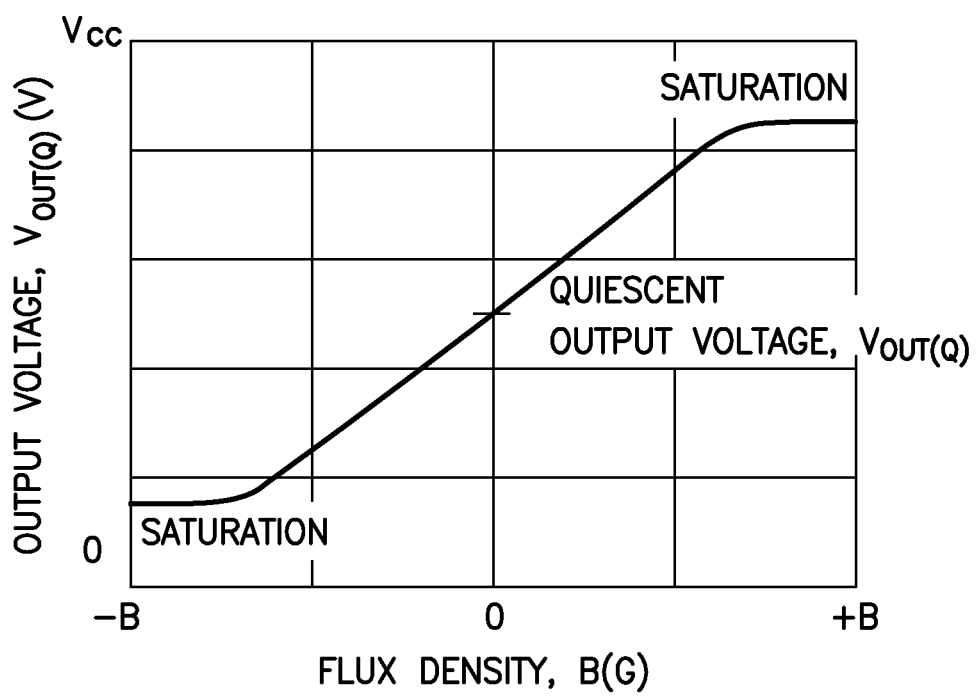
FIG. 2B illustrates a substantially linear output voltage over flux density curve for a Hall-effect sensor arrangement utilized with an exemplary embodiment of the present invention.

FIG. 2A illustrates a flux density curve sensed by a Hall-effect sensor described above as a magnet passes the sensor in close proximity. FIG. 2B illustrates the substantially linear analog output voltage response of a Hall-effect sensor used in embodiments of the present invention. Hall-effect sensors preferably convert the linear output voltage to a digital signal for output to a processor, or the like, for further processing.

Figure 3:
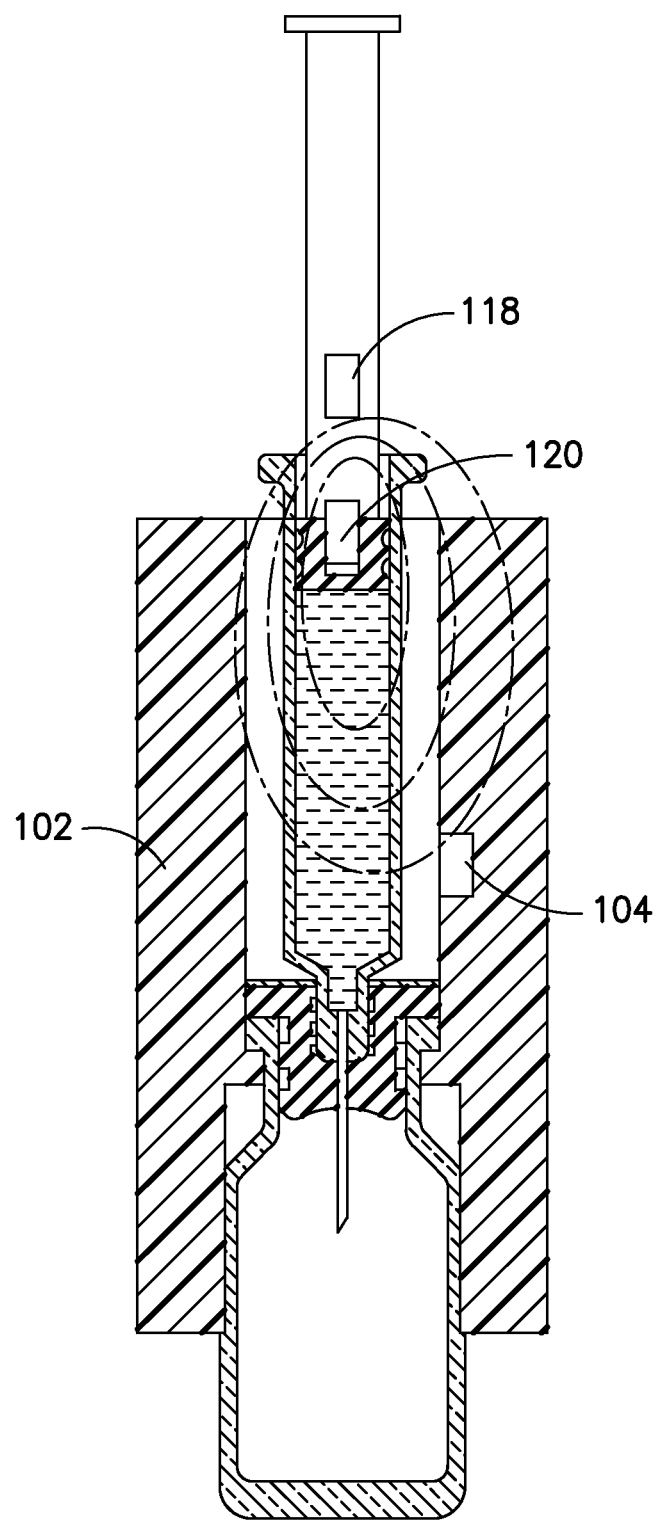
FIG. 3 illustrates an informatically enabled vial sleeve according to an exemplary embodiment of the present invention.

FIG. 3 is a cross sectional view of a syringe and vial with an informatically enabled vial attachment according to an exemplary embodiment of the invention. Depending on the total stroke intended to be sensed, multiple Hall-effect sensors may be used, but for a short stroke, only one Hall-effect sensor is needed.

Figure 4:
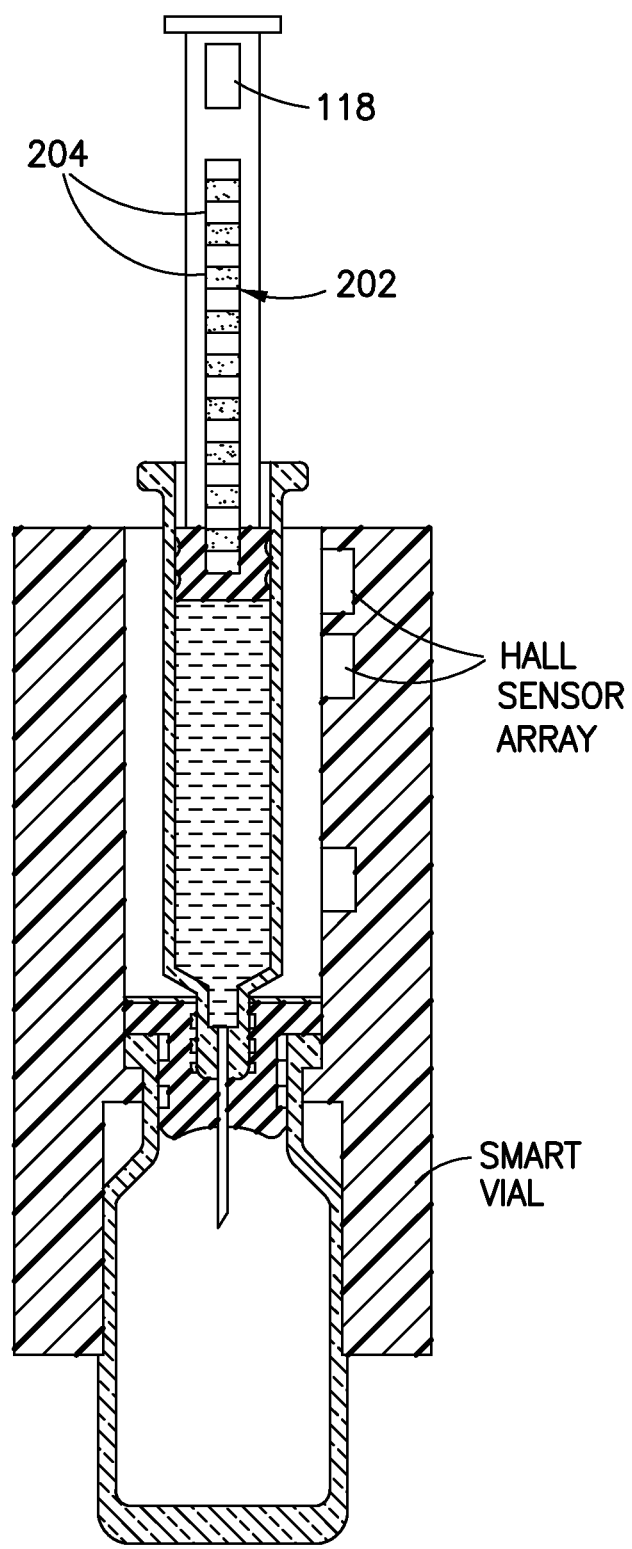
FIG. 4 illustrates an informatically enabled vial sleeve according to another exemplary embodiment of the present invention.

A second embodiment of the invention is shown in FIG. 4. A magnetic strip 202 is over-molded into the syringe plunger. The strip 202 has numerous magnetic poles 204 that repeatedly alternate from north to south over the length of the strip. As in the first embodiment, a vial attachment would include the componentry necessary to read the RFID chip, sense the position of the plunger, and wirelessly communicate the volume of insulin injected. In this embodiment, high resolution (positional accuracy) is achieved using the same basic principle as used in an optical encoder. That is, a stacked set of magnets form a series of north and south magnetic poles that are sensed in a similar manner to black and white (or opaque and optically transmissive) optical patterns on an optical encoder. The position sensor can be a single integrated circuit that incorporates multiple Hall-effect sensors, which are arranged to detect the motion of the magnetic strip with high-resolution output that can be interfaced directly to a microcontroller. Such high resolution magnetic position sensors are available from, for example, Austria Micro Systems, ams AG. In combination with a multipole strip, a single high resolution magnetic position sensor can sense pole pairs passing the face of the sensor in order to accommodate any length stroke with a single sensor. High resolution single-chip sensors with multiple Hall-effect sensors are advantageously compact and operate for both linear and off-axis rotary motion sensing. These devices offer resolutions down to 15 microns (µm). As a reference, for a 1 ml syringe with 0.478 cm internal diameter, 56 µm displacement of the plunger would equate to 0.1 units or 0.001 ml.

Figure 5:
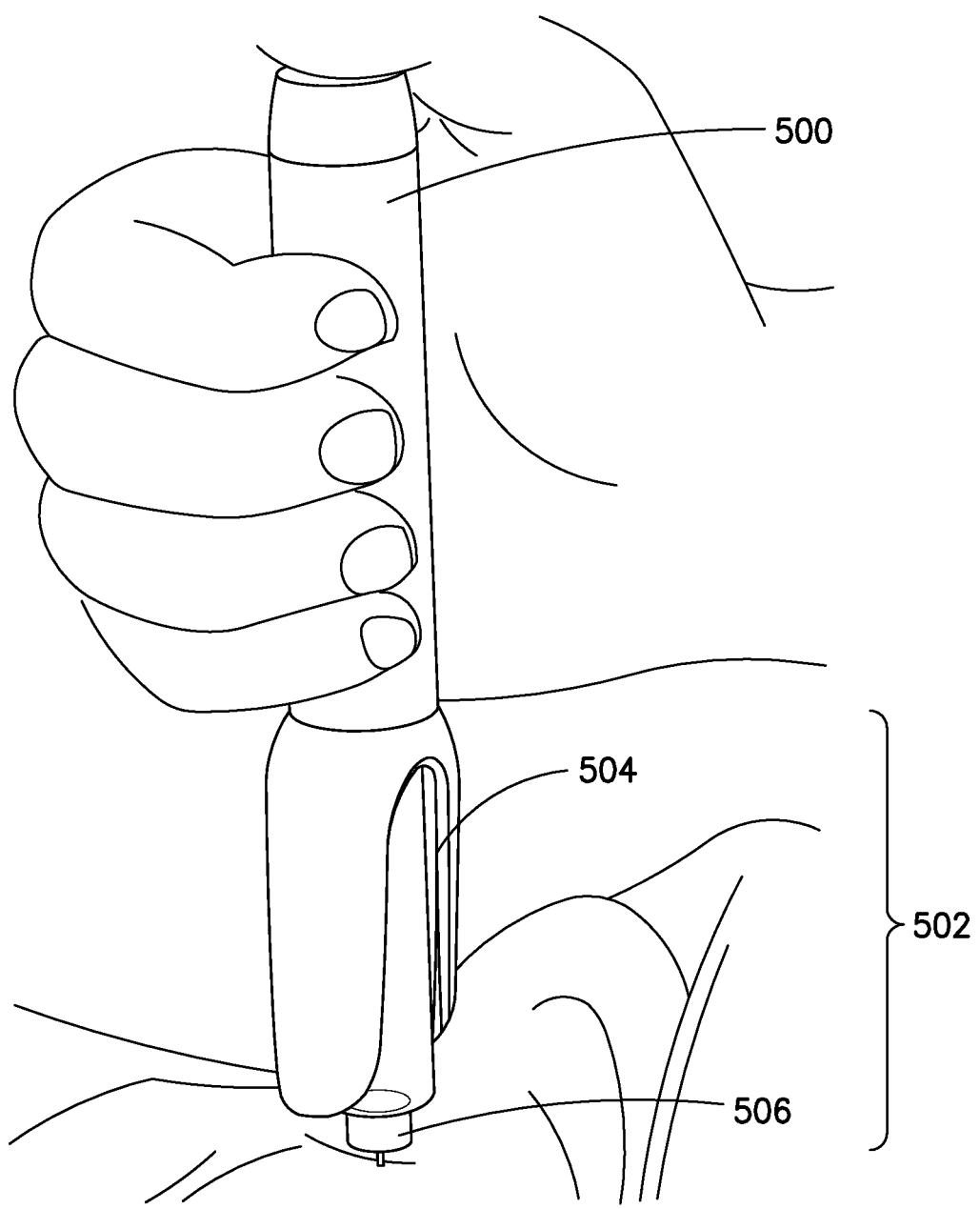
FIG. 5 illustrates a pen cap and flow sensor according to an exemplary embodiment of the present invention.

A third embodiment of the invention is shown in FIG. 5, which illustrates a disposable or reusable insulin injection pen 500. Any suitable flow sensor, including preferably Micro-Electro-Mechanical Systems (MEMS) flow sensors could be utilized to provide an informatically enabled insulin pen. One type is a MEMS micro-Coriolis mass flow meter which utilizes an oscillating tube to precisely measure the force of mass flow within the tube. A second type is a MEMS thermal time-of-flight flow sensor. In addition, a pair of MEMS capacitive pressure sensors on either side of a restriction can be used. A pen attachment 502 comprises a reusable 504 and disposable 506 portion. The reusable portion 504 is a pen cap or sleeve that attaches to the delivery end of insulin pen and is used until the insulin in the pen is exhausted. The disposable portion 506 is a plastic molded component in the shape of a small cylinder and has a MEMS flow sensor integrated into a fluidic channel through which the insulin flows. The disposable MEMS cylinder is attached to the end of the pen, and the pen needle is attached to the MEMS cylinder. A removable or retractable end cap is used to protect and expose the MEMS cylinder and allows the patient to exchange the pen needle at the time of use. The dose is preferably captured at the precise time of delivery, data is time stamped, and wirelessly transferred to a smart phone and/or the "cloud" or internet.

MEMS sensors typically come prepackaged by a manufacturer. Conventional MEMS sensors as described above contain not only the specific MEMS component which is necessarily very small, but also related electronics and circuitry. However, in embodiments of the present invention, the small MEMS component is preferably separated from the related circuitry. In this manner, the small MEMS component may be disposable, and the related circuitry can be reusable. In the embodiment shown in FIG. 5A, for example, the small MEMS component would be located in the disposable flow sensor 506, while the related circuitry would be located in the reusable pen cap 504. This arrangement has significant cost advantages for manufacturing. As an example, a conventional MEMS sensor package may cost ~$10, while the small MEMS component may cost less than ~$1. Accordingly, it is advantageous to separate the small MEMS component from the related circuitry so that the expensive portion may be reused, and the less expensive portion may be disposable. Alternately a magnet is attached or incorporated into the plunger of an insulin cartridge adapted for insertion into an insulin pen. In one exemplary embodiment a Hall-effect sensor is incorporated into a pen cap, and detects the position of the plunger after injection when the pen cap is placed back on the pen. The relative movement of the cartridge plunger before and after injection corresponds to the dose amount, which is recorded, logged and preferably transmitted to a remote device such as a cloud-based storage for further processing and feedback. In another exemplary embodiment, the Hall-effect sensor and related circuitry are located in the pen case, and the relative movement of the cartridge plunger is measured each time the insulin pen is placed back into the pen case. This embodiment has the advantage of using the large amount of space available in the pen case for the Hall-effect sensor and related electronics.

To enable the systems described herein to capture dose delivery in real time, that is, at the time the dose is being injected into the patient's tissue, all of the system elements need to be in communication at the time of dose delivery. The pen needle captures a dose in real time when the reusable sleeve is attached to provide the following functions: (1) receive the sensed data that correlates with the volume of the dose, (2) calculate the dose, (3) time stamp the dose, (4) provide power for the sensor and these functions, and (5) to also simultaneously or at a later time wirelessly communicate the dose and time stamp elsewhere in the IEO dose capture system, such as to the patient's records in the cloud. A replacement pen cap that covers the needle end of an insulin pen and senses plunger movement does sense the movement of the plunger at the exact time of delivery. A pen cap that covers the knob end of an insulin pen and senses the knob movement and travel can preferably capture the real time delivery of the dose, because all the system elements are in communication at the time of delivery.

To reduce the cost of the disposable MEMS sleeve, the componentry in the sleeve, that is, the MEMS chip and electrical contacts for power and data connections to the informatics enabled pen sleeve is minimized. This device comprises a plastic sleeve into which are assembled the MEMS chip and the electrical contacts, which are either snap fit, over-molded, or clenched by a retaining component, and a septum, which would be pierced when engaged by the pen needle. These two concepts provide additional benefits as compared to the embodiments described above because they capture the time of the actual delivery as compared to the time of plunger movement to fill a syringe or the displacement in the plunger of an insulin pen sometime after the dose has been delivered, such as when the smart pen cap is placed back onto the pen.

The above described embodiment is also applicable to an injection port, such as the Patton Medical injection port. The embodiment for use with an injection port may be completely disposable or a combination of disposable and reusable components. Any of the MEMS sensors described above could be spliced into the fluidic pathway within an injection port and the componentry and intelligence that are provided in the informatics enabled sleeve described above would be incorporated into the injection port in the outer perimeter of the port; that is, in the area surrounding the septum into which the syringe would engage. A preferred embodiment for an injection port is a disposable/reusable design in which the disposable portion includes the adhesive, the portion of the housing to which the adhesive attaches, and the components comprising the fluidic path including the MEMS sensor and the electrical connections from the sensor to the informatics enabled reusable portion, which contains all the componentry described above in the informatics enabled sleeve. As discussed above, drug identifying techniques may also be incorporated to verify the specific drug being administered.

Figure 6:
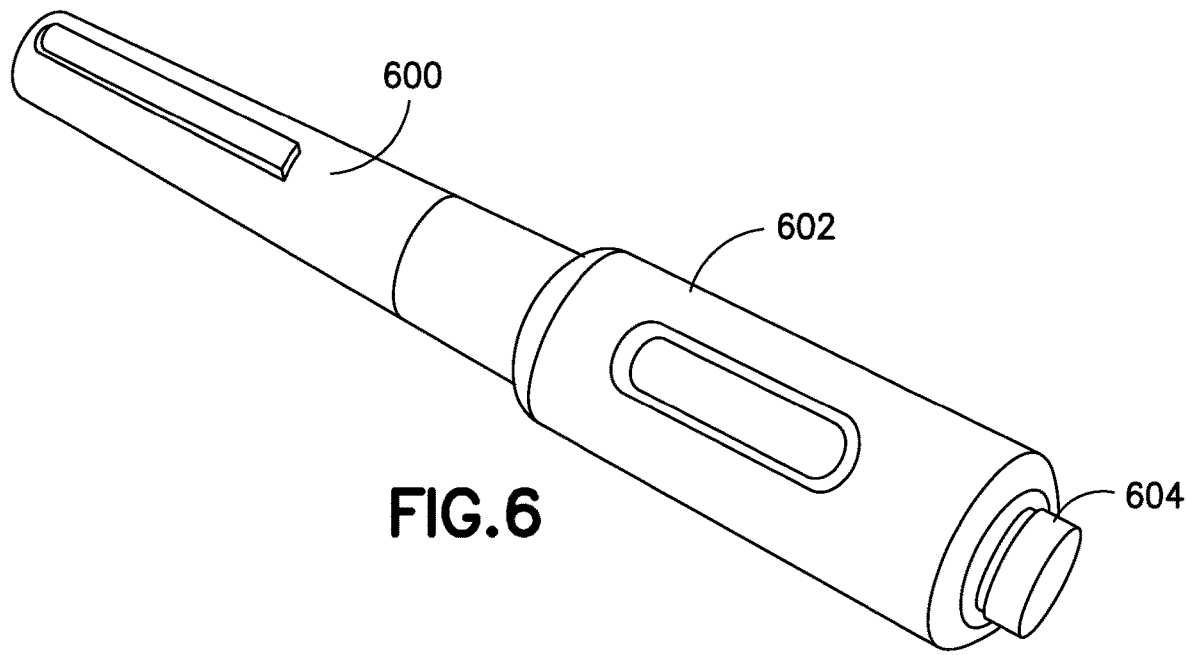
FIG. 6 illustrates an informatically enabled attachment for a reusable or disposable pen according to an exemplary embodiment of the present invention.
Figure 7:
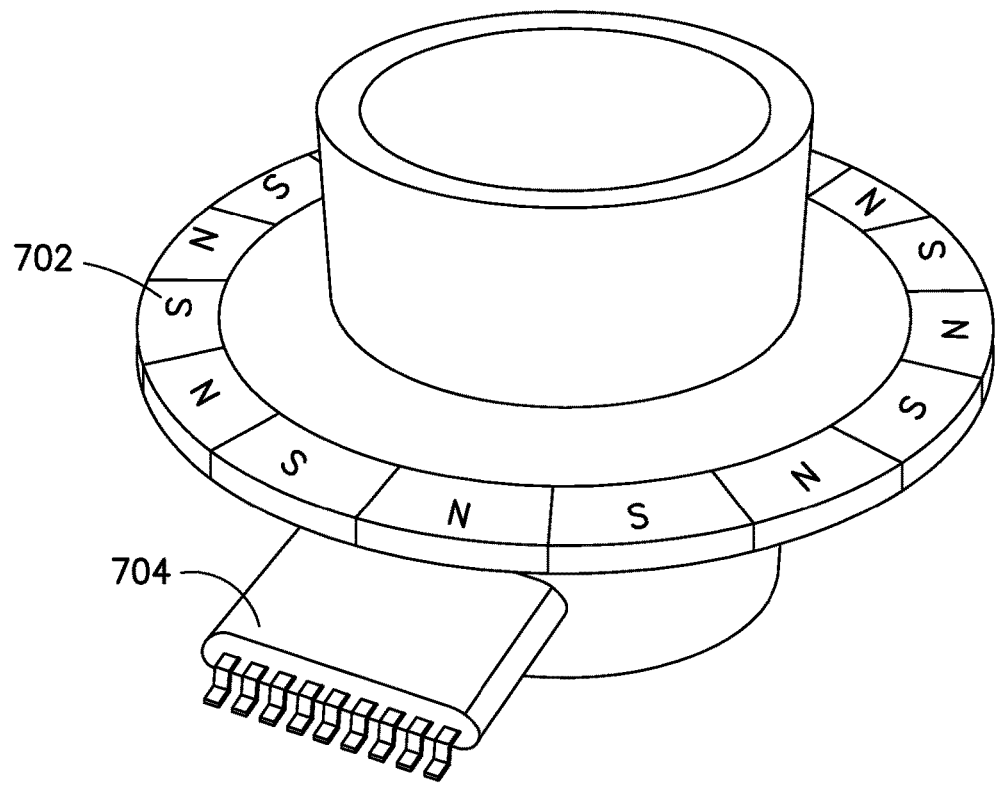
FIG. 7 illustrates a multi-pole magnetic ring and Hall-effect sensor arrangement for use with the attachment illustrated in FIG. 6.

Another embodiment of the invention is illustrated in FIG. 6, which illustrates an informatics enabled attachment 602 for either a reusable or disposable pen 600. This embodiment engages with the adjustment end of the pen. More specifically, a rotational turn knob 604 on the informatics enabled sleeve 602 engages with the adjustment knob (not shown) on the pen, and the sleeve portion 602 of the informatics enabled attachment slides over and engages with the outer diameter of the barrel of the pen. In one alternative of this embodiment, over-molded metallic splines located axially around the diameter of the knob are used for proximity sensing, similar to a ring counter arrangement that utilizes a proximity sensor to count gear teeth, or splines in this case, as they pass in front of the sensor. In another alternative of this embodiment shown in FIG. 7, a multi-pole magnetic annular ring 702 is used in combination with a Hall-effect sensor 704. The rotational motion and direction of the cap are determined with a rotational Hall-effect sensor or an MR sensor. Determining direction requires a two sensor device such as an Allegro A1233, or a four sensor chip such as an ams AS5304/5306. An AMR sensor requires integration with a single Hall effect sensor to provide direction as well as 360 degree sensing.

FIG. 8 is an illustrative embodiment of a SMART fixed dose pen, for which the intelligence in the system is reduced, i.e. because the dose has been preset and each dose is the same, only the time of actuation/delivery needs to be captured and therefore the Hall-effect sensing arrangements described above are not required. FIG. 9 is another illustration of either an adjustable or fixed dose pen. FIGS. 10 and 11 illustrate embodiments of informatics enabled mechanical patch pens. As used herein, the term "patch pen" refers to a body worn device providing insulin delivery only in a fixed dose each time the user manually actuates the device, primarily utilized for prandial insulin delivery. Preferably a magnetic or metallic flag is incorporated into the mechanization or linkage within the mechanical patch pen. An informatics enabled attachment is integrated into the patch pen, in which case it is disposable, or may be in the form of a separate element that engages to the patch pen, in which case it is reusable. In one embodiment a motorized "pump engine", that is, a fluid driver used to transfer insulin from the reservoir to the injection/infusion site, delivers 2.0 units per cycle. The motorized pump engine is described in further detail in U.S. Provisional Patent Application No. 61/976,631, filed Apr. 7, 2014, the entire contents of which are hereby incorporated by reference. This pump engine is modified to eliminate the motor and provide mechanization that enables the user to drive the pump engine by squeezing or depressing a button or buttons located on the exterior of the pump, and includes a magnetic or metallic flag located on the linkage within the patch pen, which is sensed by the informatics enabled attachment each time 2.0 units of insulin is delivered manually by the user. Any of the magnetic sensing solutions described above, optical sensing, or any suitable sensing technology, may be utilized for sensing. Additionally, the same pump engine with similar manually driven mechanization may be utilized to actuate delivery in an insulin (or other drug) pen and provides a fixed dose with each actuation, and records the amount and time of each dose.

Figure 12:
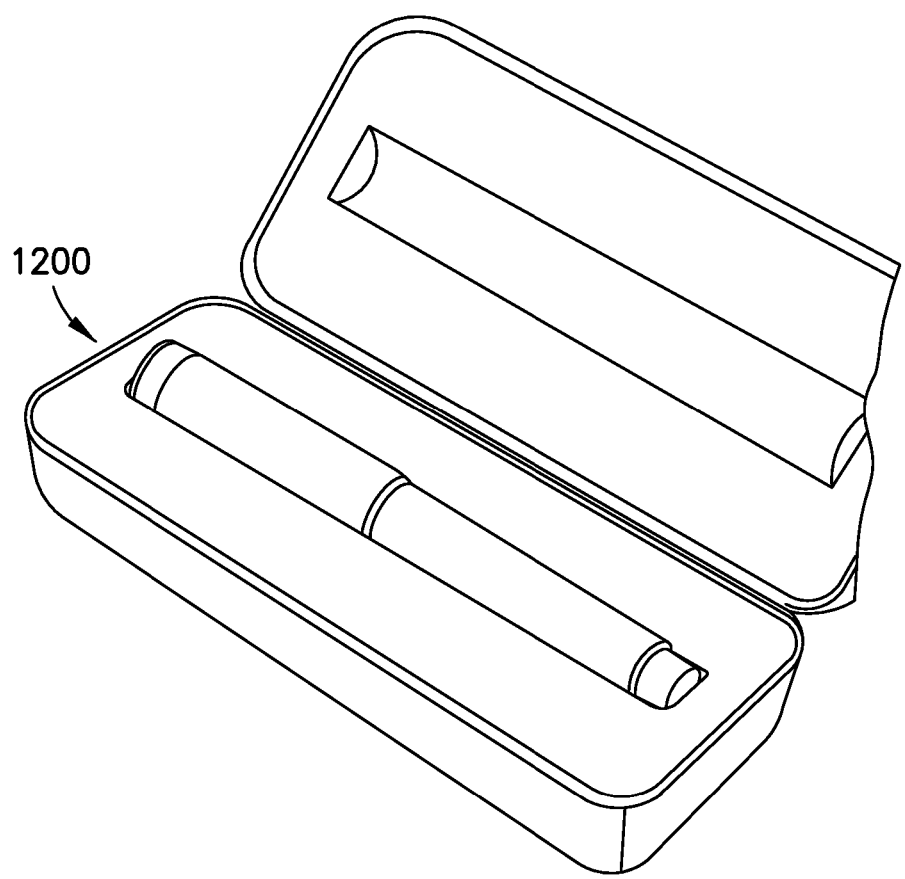
FIG. 12 illustrates an informatically enabled pen case according to an exemplary embodiment of the present invention.

Pen cases provide a clean, sealed container in which users can store their injection delivery device and consumables, such as an insulin vial, insulin pen or syringes, pen needles, lancer and lancets, and alcohol swabs. Pen cases can be either rigid, that is, having a hard exterior shell, similar in design to a jewelry box, or flexible, that is, a flexible pouch, similar to a pencil case. FIG. 12 illustrates an informatics enabled rigid pen case 1200 according to another embodiment of the present invention. The informatics enabled pen case stores the patient's syringe or insulin pen when the device is not being used. A nest or cavity within the pen case is used to register or locate the pen, each time the user places the pen into the case. Each time the pen case is closed, the Hall-effect sensors within the pen case determine the relative position of the plunger and thereby determining the dose delivered to the patient. For a reusable pen, the insulin cartridge would need to be modified to include a magnetic or metallic flag, such as a washer shaped element with Pressure Sensitive Adhesive (PSA) on one side, that is pressed onto the exposed surface of the stopper in the cartridge, and potentially an RFID chip or some other means, such as a bar code, to convey the ID of the insulin cartridge and the type and concentration of the drug. The magnetic or metallic element is preferably incorporated into the stopper/plunger during manufacturing. In operation, each time the pen is placed into the case, sensors in the pen case scan to detect the position of the stopper and compare the current and previous positions to determine the dose delivered. Data is time stamped, stored within the case and periodically transferred to a smart phone and/or the cloud. One advantage of the pen case is the volume of space available in which to configure the informatics enabling components, which can reduce the cost and improve the performance of the solution by incorporating inexpensive, high-performance components such as off-the-shelf (OTS) batteries, rigid PCBAs, large footprint antennas, an RFID reader, a large user interface (UI) that accepts input from a touch screen, keypad, or from audible commands and provides a display with data, alerts, and warnings for the patient. To enable the use of a flexible pen case, two magnets are incorporated into the syringe or insulin pen, one fixed and the other on the moveable plunger. Each time the pen is placed into the flexible case, the line and relative distance between the two magnets is sensed allowing the dose to be calculated. This concept is also applicable to informatics enabled cartridges utilized in reusable pens and informatics enabled pens that are stored in the pen case, as described above. It will be appreciated that any suitable sensing technology may be utilized, and in particular, magneto-inductive sensing is one alternative suitable for sensing in a pen case. A magneto-inductive displacement sensor operates by using an inductive sensor coil to detect the change in magnetic field as the magnet moves. It is used in head-on sensing with a range of up to 60 mm depending on magnet size, which is used to detect the position of a magnet incorporated into the plunger piston of an insulin pen or syringe after is placed into a pen case.

Figure 13:
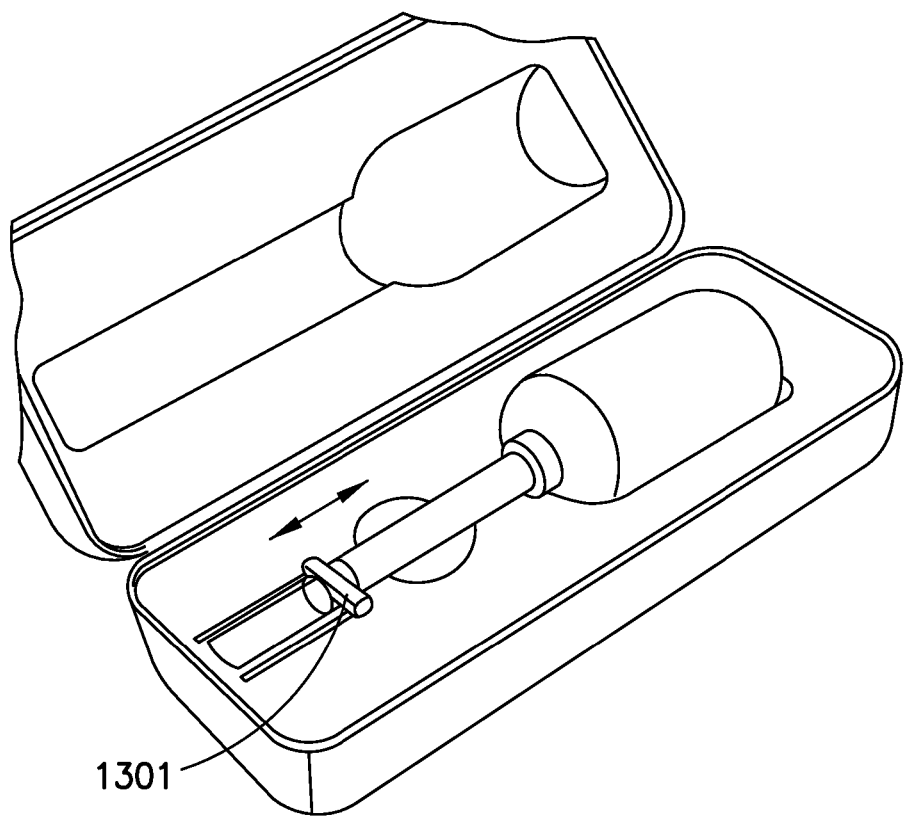
FIG. 13 illustrates an informatically enabled pen case according to another exemplary embodiment of the present invention.

FIG. 13 illustrates an informatics enabled pen case that is further enabled to draw the dose into the syringe. This embodiment of the pen case includes a clamping system 1301 to register the syringe, that is, to precisely locate the syringe on two axes, a nest or cradle to register the insulin vial, and a second clamping system to grip and control the movement of the syringe plunger. In operation, the user places a syringe into the nest adjacent to an insulin vial within the pen case, closes the case, and enters the dose to be delivered into the UI. The two separate clamping arrangements within the case grip the syringe. The first clamp system grips the syringe and advances the syringe to engage the syringe needle into the vial of insulin. The second moves the plunger to draw in the correct dose of insulin. The syringe is retracted from the vial either automatically or by the patient. The same arrangement may be utilized to create a positive pressure within the insulin vial. Orientation or gyroscopic sensors could be used to confirm proper orientation of the pen case for air purge or insulin draw and prompt the user to orient the pen case accordingly. An exemplary smart pen case is described in U.S. Pat. No. 7,901,383, the entire contents of which are hereby incorporated.

As in all embodiments described herein each injection is preferably recorded and time stamped in an electronic logbook, and transferred periodically to a peripheral monitor device such as a laptop computer, cell phone, or other user interface, for review by the patient. Alternately the data could be conveyed via a computer network to and from the cloud to the patient's health care providers. The functionality of the informatics enabled insulin pen case could be further expanded by incorporating auxiliary devices into the system, such as vital signs monitors, fitness monitors or activity trackers, and Continuous Glucose Monitors (CGMs).

Another embodiment takes the form of an "All-In-One" or combination device. One example of an all-in-one device available on the market is the Dario, by LabStyle Innovations. The Dario integrates a glucose meter, lancet, strip dispenser, and phone application for either IOS or Android into a compact device. Like the pen case embodiment described above, an all-in-one device has sufficient size and volume to incorporate informatics enabling componentry described above to allow an informatically enabled insulin pen or syringe to be attached, that is, by providing a nest or holster for the pen or syringe to be physically and electrically engaged to the all-in-one housing. In this case, the connection provides retention of the pen or syringe and transfer of data. Such a device is described, for example, in U.S. Published Application No. 2011-0054390, the entire contents of which are hereby incorporated by reference. Alternatively, a wireless communication solution such as low energy Bluetooth (BLE) or Near Field Communication (NFC) could be utilized to communicate directly to a Smart phone. An example of a smart phone device communicating with other on body devices in a personal area network is described in U.S. Published Application No. 2011-0022025, the entire contents of which are hereby incorporated by reference.

Another embodiment is an informatics enabled insulin cartridge that is used in conjunction with an informatics enabled reusable pen. The insulin cartridge is modified to include a magnetic or metallic flag, such as a washer shaped element with Pressure Sensitive Adhesive (PSA) on one side, that is pressed onto the exposed surface of the stopper in the cartridge, and an RFID chip or some other means, such as a bar code, to convey the ID of the insulin cartridge, and the specific drug type and concentration. The cartridge would work in conjunction with an informatics enabled attachment for a reusable pen. Alternately, the magnetic field strength could be used to distinguish between different cartridges, eliminating the need for an RFID chip on the disposable device and an RFID reader within the informatics system. The cartridge is preferably modified during the manufacturing process, following the filling process, or by the patient, either manually or automatically as part of a cartridge filling process designed for home use.

Figure 14:
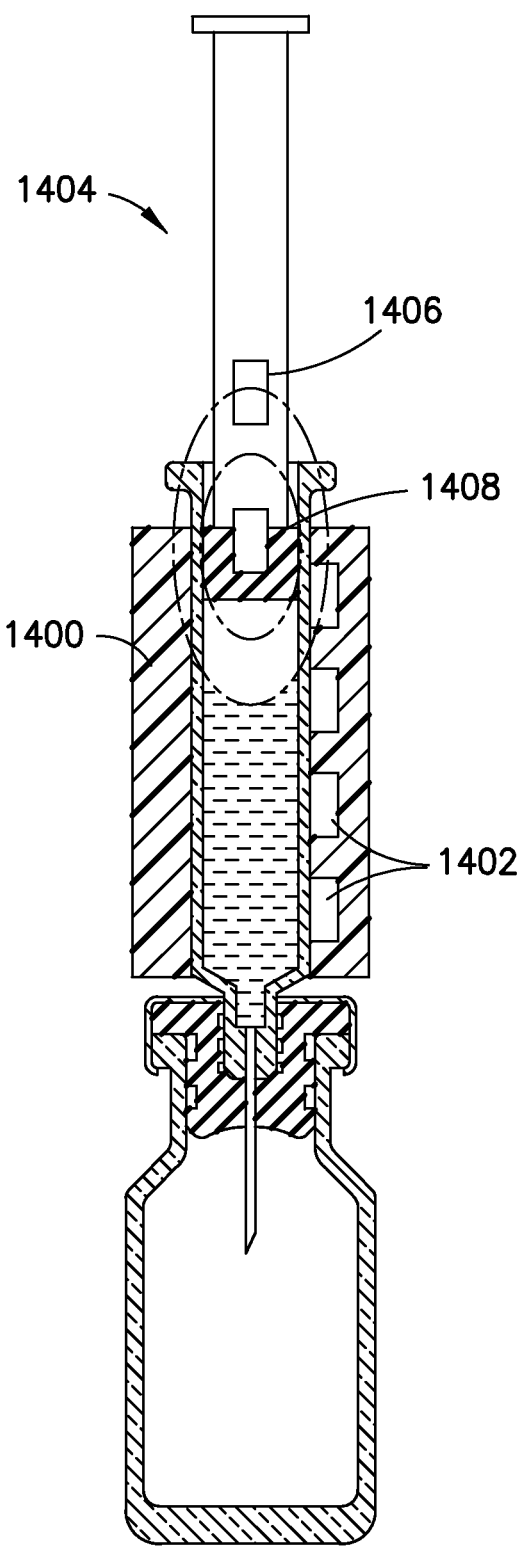
FIG. 14 illustrates an informatically enabled syringe sleeve according to another exemplary embodiment of the present invention.

FIG. 14 illustrates an informatically enabled syringe sleeve according to an exemplary embodiment of the invention. The syringe sleeve 1400 includes a plurality of magnetic position sensors 1402. The syringe 1404 has an embedded RFID chip 1406 and a magnet 1408 that is sensed by the Hall-effect sensors 1402 to determine a dose amount. Of course, as will be appreciated by one of ordinary skill in the art, any suitable type of MEMS sensing such as those discussed herein may be used in place of magnetic position sensing.

Figure 15:
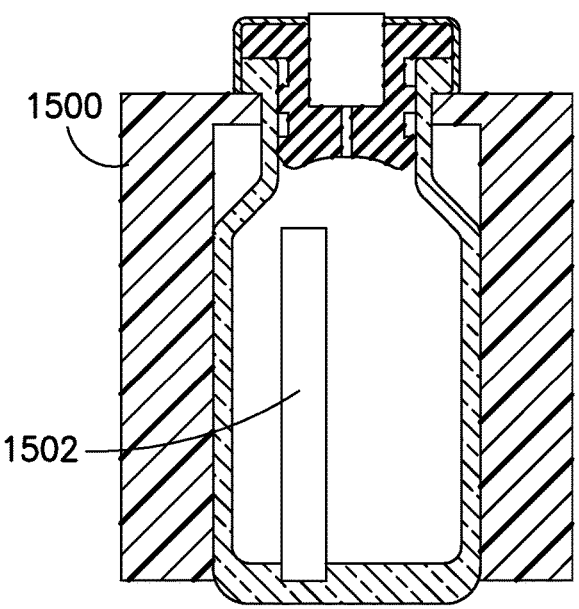
FIG. 15 illustrates an informatically enabled vial sleeve utilizing capacitance sensing according to another exemplary embodiment of the present invention.

In another embodiment, external electrodes are attached to the insulin reservoir and a variable capacitance value is sensed based on the fluid level of the reservoir. Electrodes are preferably printed onto any insulin reservoir during manufacturing, and may also be manufactured as a strip that is attached to an insulin reservoir. Alternatively, as shown in FIG. 15, an informatics enabled sleeve 1500 is provided with the electrodes 1502 provided on the inside diameter and which would contact the reservoir when attached to the pen, syringe, vial or patch pump. The electrode 1502 may be printed onto the sleeve or manufactured in any other suitable manner. The electrode 1502 preferably spans a dimension that corresponds to the volume of insulin in the vial. In this embodiment, the sleeve 1500 and strip 1502 are advantageously re-usable. In another embodiment of the informatically enabled insulin vial, the electrodes of a capacitance sensor are incorporated into the vial attachment, such that when the vial attachment is engaged with the vial, the electrode strip is in intimate axial contact with the vial.

Figure 16:
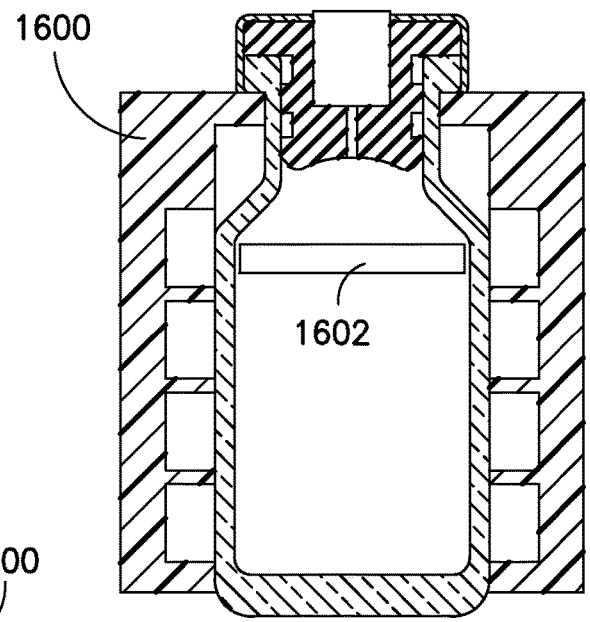
FIG. 16 illustrates an informatically enabled vial sleeve, according to another exemplary embodiment of the present invention.

FIG. 16 illustrates an informatically enabled vial sleeve 1600 according to an exemplary embodiment of the present invention. As illustrated, a floating magnetic ring 1602 is provided inside a medicine vial 1604. The ring magnet outer diameter is slightly smaller than the inner diameter of the vial so that the ring freely moves within the vial according to the fluid level within the vial. The ring magnet 1602 is preferably placed into a drug vial prior to sealing the vessel. A typical insulin vial may also be modified to accommodate a rigid magnetic ring, or a flexible magnetic ring may be wrapped in a coil, inserted into a vial through a standard vial neck, allowing the coil to unwind after insertion to a diameter that is smaller diameter than inner diameter of the vial. In the case of an insulin vial, the ring magnet is preferably coated with an insulin compatible material, such as a polymer, which is compatible with insulin and of sufficient thickness and overall buoyancy to enable the ring to float. As illustrated, the level of the ring is sensed by a linear magnetic position sensor, such as a Hall-effect sensor.

Figure 17:
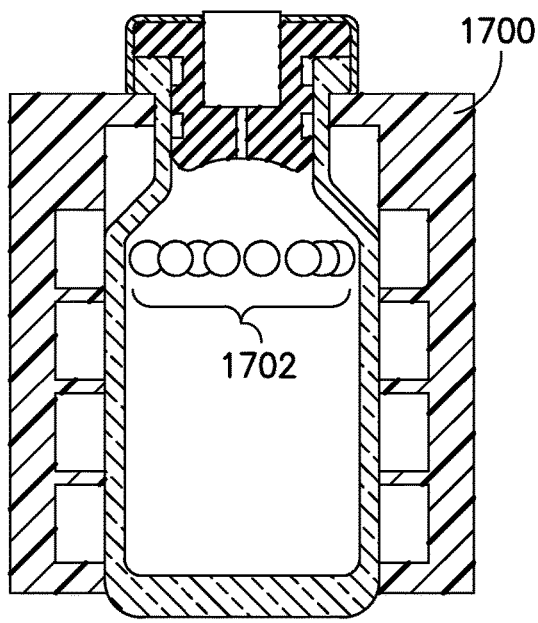
FIG. 17 illustrates another informatically enabled vial sleeve, according to another exemplary embodiment of the present invention.

FIG. 17 illustrates another informatically enabled vial sleeve 1700 according to an exemplary embodiment of the invention. In this embodiment, floating magnetic beads 1702 are utilized to sense the level of fluid in a drug vial, such as an insulin vial 1704. A smart vial sleeve 1700 is provided an attached to the medicine vial 1704. The vial sleeve 1700 senses the layer of magnetic beads floating on the surface of the insulin. The beads are of sufficient diameter that they are unable to be drawn into a dose. That is, the beads 1702 are larger in diameter than the needle or cannula or a syringe used to draw insulin from the vial. Advantageously, a user can add the magnetic beads 1702 to any medicine vial post-manufacture, to enable the smart vial sleeve 1700. In one embodiment, the magnetic beads are added to an insulin vial during the filling process in manufacturing. In another embodiment, the filled insulin vial is shipped together with a syringe filled with magnetic beads, the syringe preferably having a large cannula to inject beads into vial. The cannula of the syringe or other device used to draw insulin from the syringe is smaller than the beads to prevent beads being drawn into the injection device. The number of magnetic beads used is preferably sufficient to substantially cover the majority of the surface of the liquid medicine inside the vial. The vial sleeve attachment utilizes a linear magnetic position sensor, such as a Hall-effect sensor, MR or AMR sensor to detect the level of fluid remaining in the vial according to the position of the floating magnetic beads within the vial.

Figure 18A:
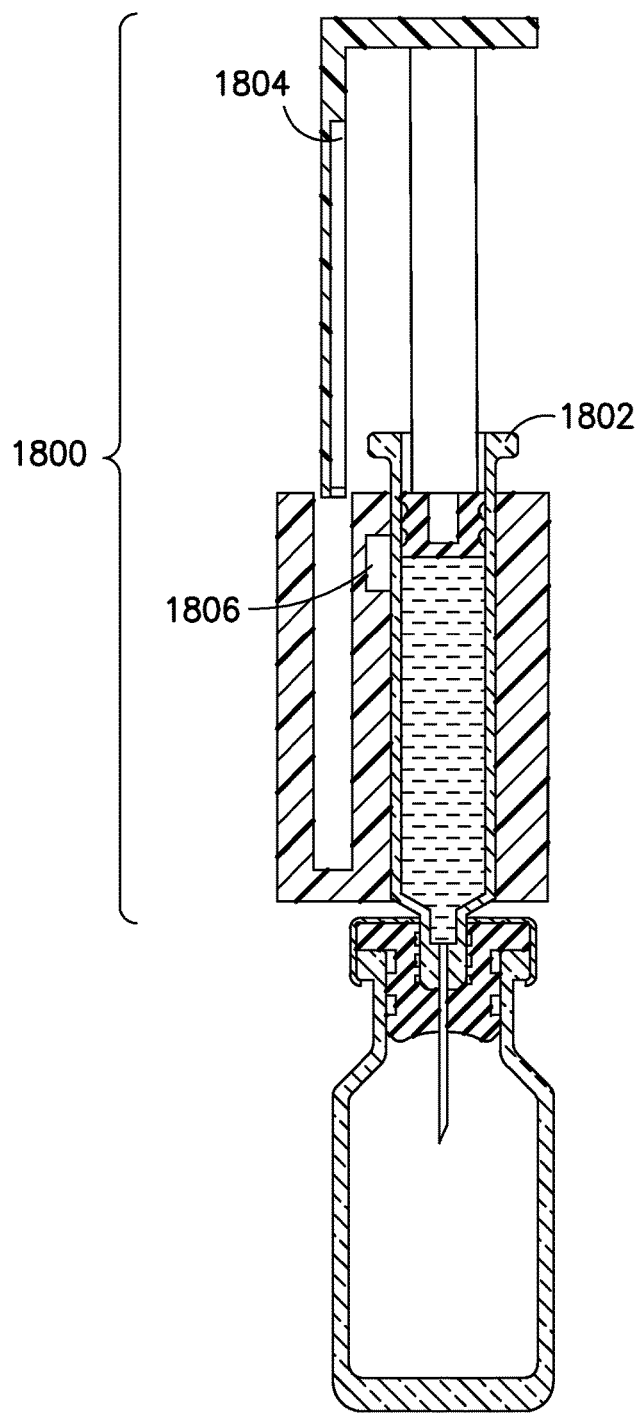
FIGS. 18A and 18B illustrate a linear magnetic position sensing arrangement attached externally to a syringe according to an exemplary embodiment of the invention.
Figure 18B:
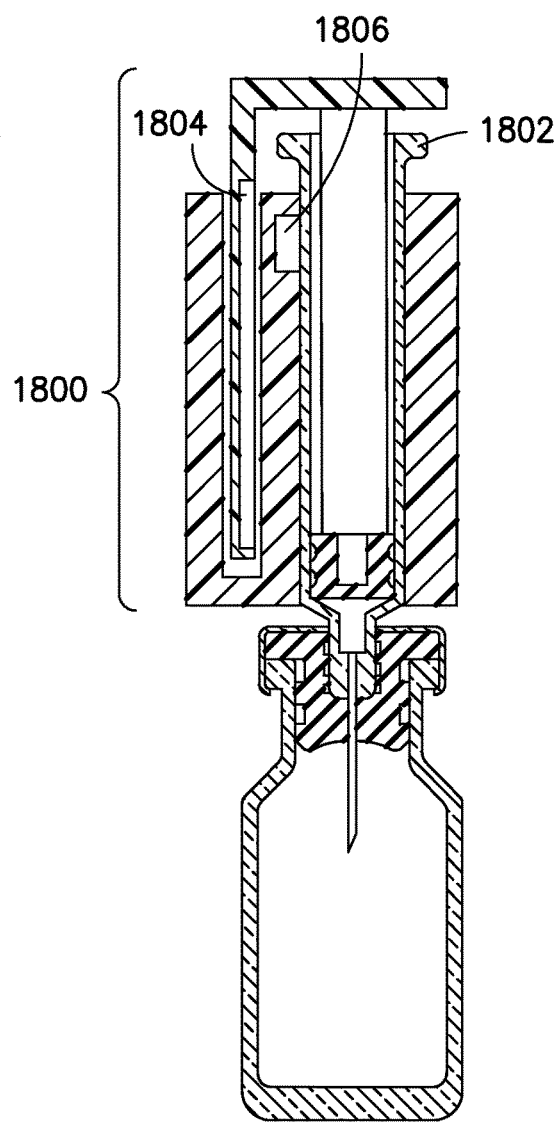

FIGS. 18A and 18B illustrate a linear magnetic positioning arrangement 1800 attached externally to a syringe 1802 according to an exemplary embodiment of the present invention. The syringe attachment 1800 conveniently attaches to a syringe 1802, so that a standard syringe may be utilized without modification. A first attachment comprises at least one magnet 1804 that attaches to the syringe 1802, and a second attachment comprises a linear magnetic position sensor 1806, such as a Hall-effect sensor, an MR sensor or an AMR sensor, to detect the position of the magnet(s) 1804. The first attachment 1804 connects to the syringe plunger and the second attachment 1806 connects to the syringe barrel, such that the movement of the plunger is tracked to determine the dose delivered. The smart syringe attachment 1800 preferably recognizes the "home" position of the plunger, that is, the position where the plunger is fully advanced and no fluid delivery is possible. In practice, the syringe plunger may be refracted and advanced many times during a single dose delivery cycle. To identify the movement associated with the dose delivery from other plunger movements, such as the movements used to inject air into the vial, the smart attachment 1800 analyzes the complete cycle of plunger movements each time a syringe is used, and identifies the dose delivered from the final movements, when the plunger advances to the home position for the final time, and from other sensed elements in the dose delivery cycle.

Figure 19A:
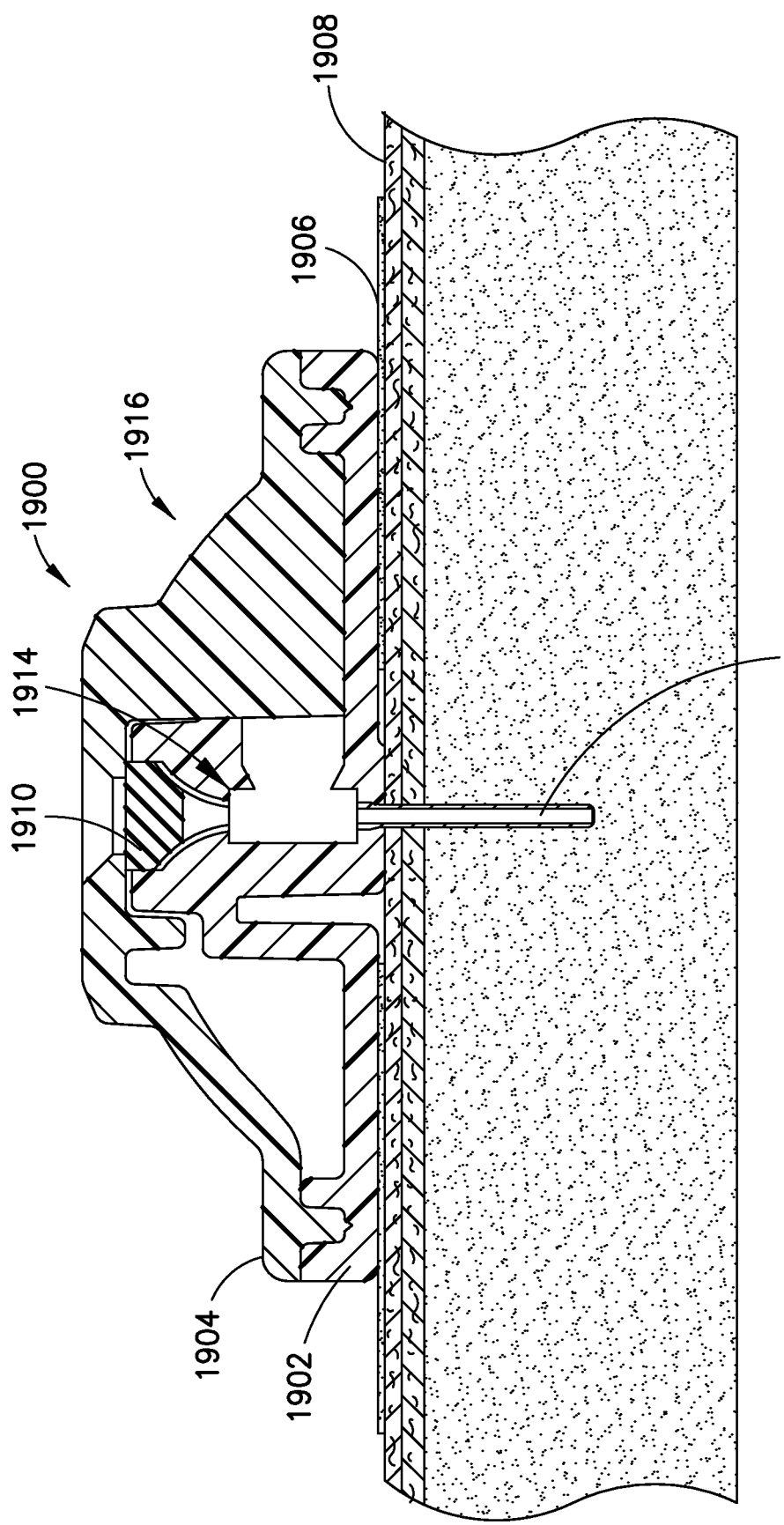
FIG. 19A-19D illustrate an informatically enabled injection port.

FIG. 19A illustrates a smart injection port 1900 according to an exemplary embodiment of the present invention. The exemplary smart injection port preferably comprises a lower housing 1902 and an upper housing 1904. The lower housing includes an adhesive surface 1906 to facilitate attachment of the smart injection port to a patient's skin 1908. A septum 1910 is arranged between the upper and lower housings 1902, 1904. The septum 1910 provides access to a cannula 1912 that is inserted into a patient's skin 1908. The septum 1910 may be pierced by an injection syringe, or the like, to inject insulin into the patient through the cannula 1912 without requiring a needle stick for each injection. The smart injection port 1900 includes a MEMS flow sensor 1914 arranged in the flow path between the septum 1910 and the cannula 1912. MEMS flow sensor 1914 is electrically connected to related electronics located in area 1916 of the injection port 1900. The related electronics include a power supply, processor, and wireless transceiver for transmitting flow measurements to a remote device. Housing 1902 is preferably disposable, and includes the MEMS flow sensor 1914. Housing 1904 is preferably reusable, and includes the related electronics in area 1916. The MEMS flow sensor is preferably a thermal time of flight sensor, but any suitable MEMS flow sensor could be employed.

Figure 19B:
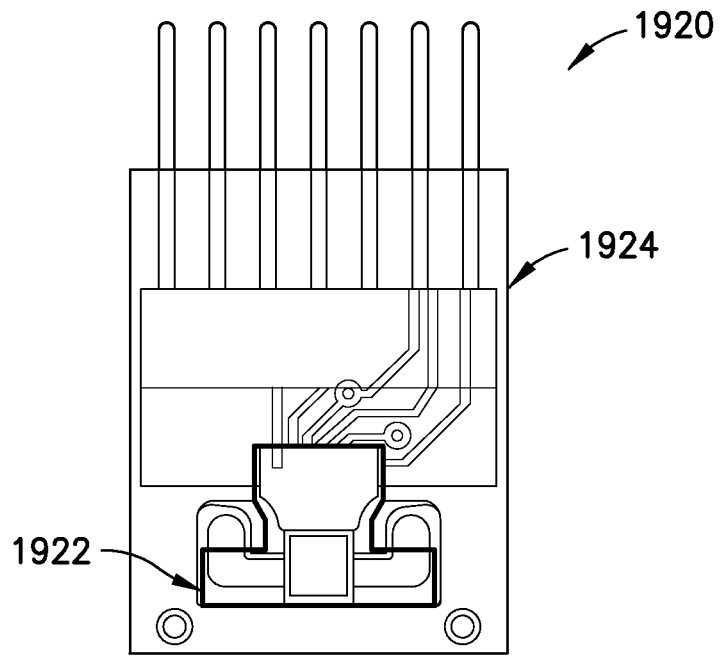

FIG. 19B illustrates a conventional single-package MEMS flow sensor 1920. In the single package MEMS flow sensor, the actual MEMS printed sensor 1922 is combined with related electronics 1924. The MEMS printed sensor 1922 includes at least one heater, at least one sensor and a flow channel through which a fluid such as insulin flows. The related electronics 1924 are electrically connected to the MEMS printer sensor 1922 within the single package, and include an integrated circuit, processor, power supply, wireless transceiver chip, and the like.

Figure 19C:
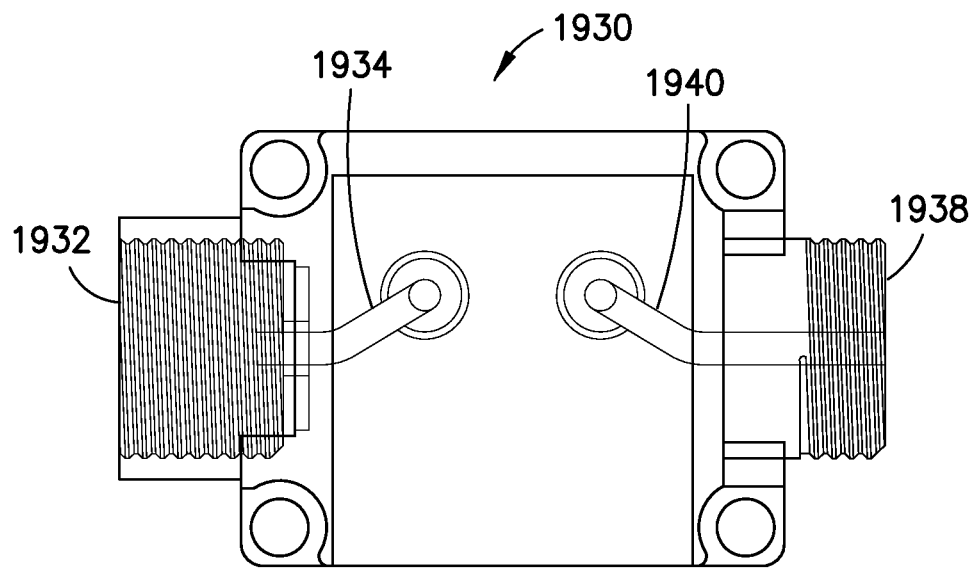
Figure 19D:
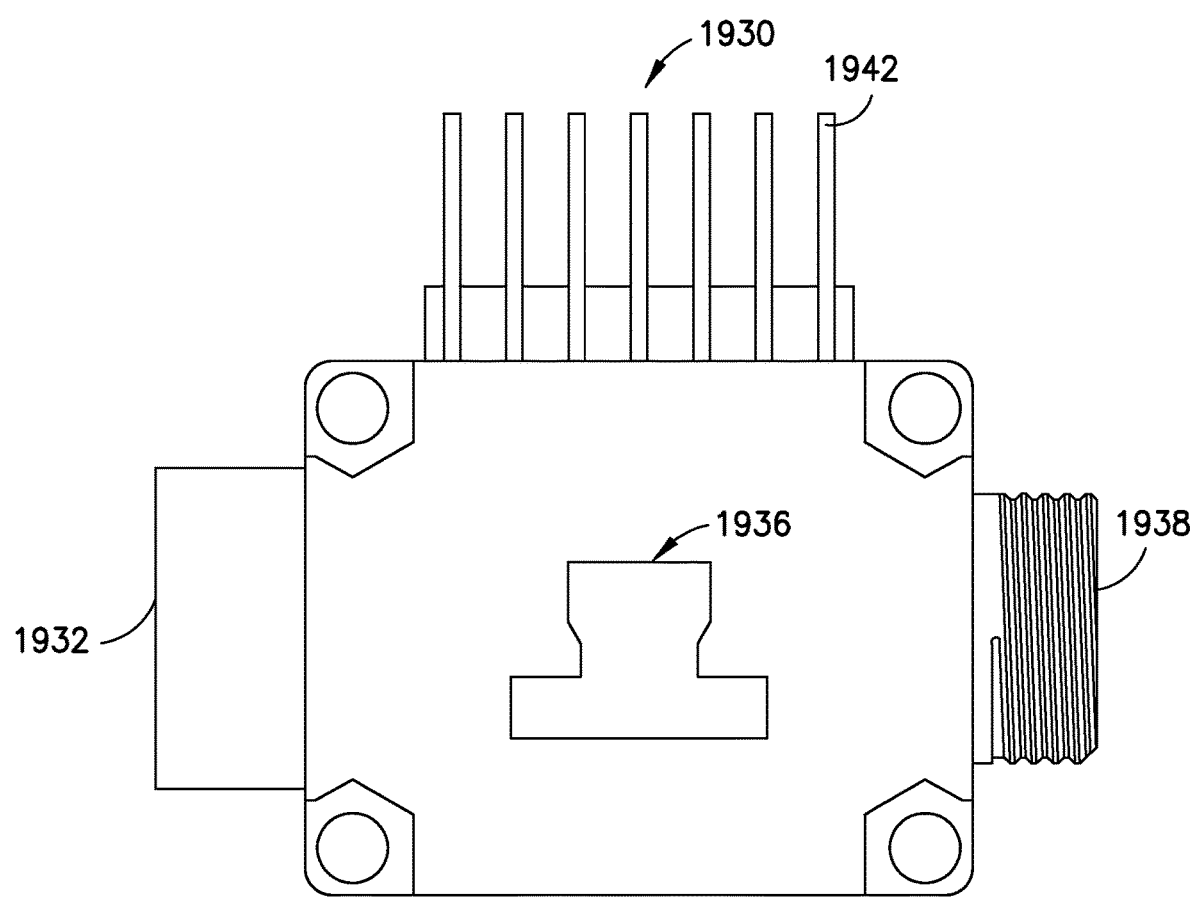

FIGS. 19C and 19D illustrate an improved MEMS flow sensor 1930 that includes only relatively low cost disposable parts that should be replaced with each use due to contact with insulin or the like. As illustrated in FIG. 19C, the MEMS flow sensor 1930 includes an input side 1932 with an input flow tube 1934 through which liquid such as insulin flows to the MEMS printed sensor element 1936 (shown in FIG. 19D). The MEMS flow sensor 1930 further includes an output side 1938 with an output flow tube 1940 through which liquid such as insulin flows from the MEMS printed sensor element 1936 to downstream elements. As shown in FIG. 19D, the MEMS flow sensor 1930 includes electrical contacts 1942 for connecting the MEMS printed sensor element 1936 to related electronics, as described above. The related electronics include, for example, an integrated circuit, a processor, a power supply, and a wireless transceiver chip. Because the related electronics are separately packaged, they may be incorporated into a reusable element in an exemplary medication delivery device, thus significantly reducing overall cost.

Figure 20:
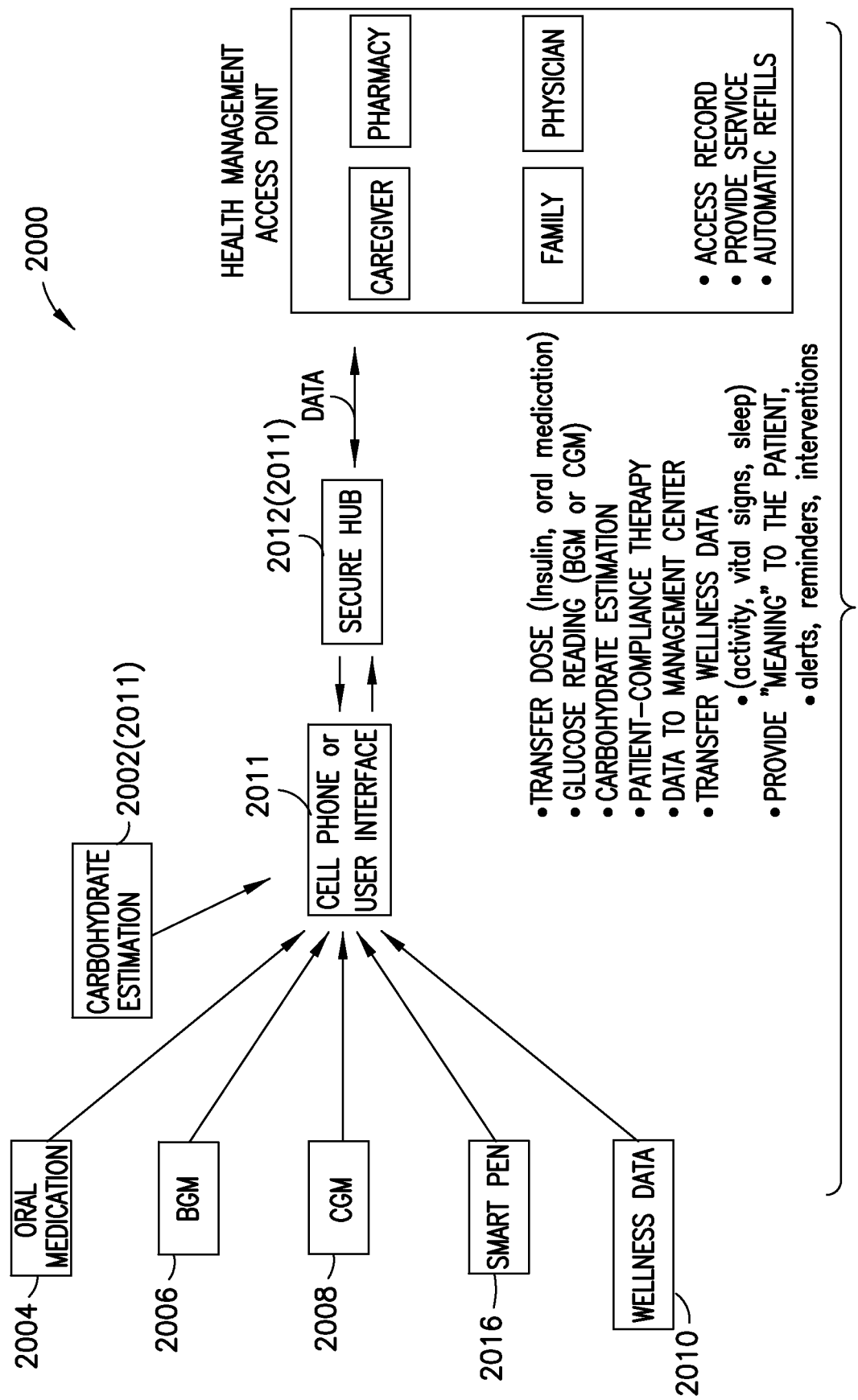
FIG. 20 illustrates a wireless communication system including an informatically enabled medicine delivery device according to an exemplary embodiment of the present invention.

FIG. 20 illustrates a system according to an exemplary embodiment of the present invention. The system 2000 includes various components for capturing data and at least one calculating element for receiving data and performing calculations on the data. As illustrated the exemplary system preferably includes a carbohydrate input element 2002, an oral medication input element 2004, and blood glucose monitor (BGM) 2006 and/or a continuous glucose sensor (CGM) 2008. The system preferably includes a wellness data input element 2010. Finally the system preferably includes one of the various embodiments of dose capture device 2016 as described herein. As an example, a smart pen 2016 is illustrated. Together these devices input the significant relevant data needed to monitor a patient with a disease such as diabetes for improved diabetes management. An exemplary carbohydrate input device 2002 can be an app running on a user's cellphone 2011, or the like, which lets the patient input food and drink consumed. Similarly, the same or a related app can serve as an oral medication input element 2004 and permit the user to track oral medications ingested. In addition, the oral medication input element 2004 can be automated to alert the user to take medication, and to confirm and automatically transmit data related to the oral medication taken to the secure hub 2012. The BGM 2006 and/or CGM 2008 preferably communicate blood glucose readings directly to a data hub device 2012. Wellness data can be input by a separate device 2010 or by a related or the same app as described above. The dose delivery information device 2016 according to exemplary embodiments described herein, preferably delivers dose information, such as insulin injected into the patient, in real or near real time. All of the data is received locally by a smart device, such as a cellphone 2011 running the app or apps discussed above. It should be appreciated that while the carbohydrate input element 2002, the oral medication input element 2004, the wellness data input element 2010, the cellphone 2011, and the data hub 2012 are shown as separate elements, all or any combination of them may be combined into a single cellphone or similar computing device. Data is analyzed and calculations are performed locally by the smart device and/or smart phone 2011, and the data hub 2012 is used to transmit data securely, that is, encrypted, to a remote server such as a cloud storage server, and in turn to perform calculations on all of the data received, provide feedback to the user, send all or a portion of the data to a remote health management access point 2020, such as cloud storage, where the information can be accessed by healthcare stakeholders, such as the patient's physician, caregiver, pharmacy, and family. Conversely, alerts, reminders, and interventions can be provided by the user's network, e.g. an HCP, securely through the data hub 2012.

An embodiment of the present invention includes several features. The first is dose capture, which measures the volume of insulin delivered and a time stamp. This information is preferably captured in a manner that is transparent to the patient. The second is data transfer, which occurs at different interfaces, such as between the dose capture device and the user interface (UI), or between the patient and health care provider. Additional functions include data transfer to the patient, health care provider, such as a PCP, endocrinologist, or nurse educator, or another risk bearing entity, such as a family member, or diabetes support network. BGM data/CGM data may be incorporated, measured and time stamped. Life style data such as diet and exercise may be captured and considered. Embodiments of the present invention preferably are compatible with fitness monitors and nutrition Apps. Embodiments of the invention preferably include additional intelligence to provide helpful alerts, warnings, recommendations, interventions, intelligent decision making, such as trend analysis, predictions, and therapeutic modifications. Finally, embodiments of the present invention may incorporate or consider oral medication. Preferably, embodiments of the invention are compatible with an oral medication adherence device, such as a Smart pill container.

Although recent advances in infusion pump therapy have reduced the growth rate of the multiple daily injection (MDI) segment, the overwhelming majority of diabetic patients on insulin therapy continue to receive delivery through MDIs, and primarily with disposable insulin pens.

The cost of incorporating the necessary components to informatically enable a disposable syringe or insulin pen could be reduced where the informatically enabled portion of the device could be reused, such as in a replacement cap on an insulin pen, or the number of uses of the disposable device could be increased such that the added cost per use would be acceptable, such as a exchanging needle cannulae into a "universal" needle hub. Such a hub is described, for example in U.S. Published Application No. 2012/0041417, the entire contents of which are hereby incorporated by reference. The increase in size of the device is another consideration. Adding an appendage to an insulin pen or modifying the pen cap and creating a larger, less appealing envelope, such that the modified device needs to be carried in a purse or pack is undesirable. Another issue is creating a universal solution that can be utilized with most currently marketed insulin pens.

A preferred embodiment that satisfies the above criteria is an informatics enabled insulin pen case, which could utilize a number of different methods to capture the delivered dose, such as taking the weight of the insulin pen each time the pen is placed in the case and the case is closed. The case provides sufficient space to incorporate the necessary electronics, and by having potentially more space than needed, the design can be tailored to utilize inexpensive electronics, such as a rigid PCBA, a disposable battery that has been commoditized, large footprint antenna options for low power data transmission, and ease of assembly.

Figure 21:
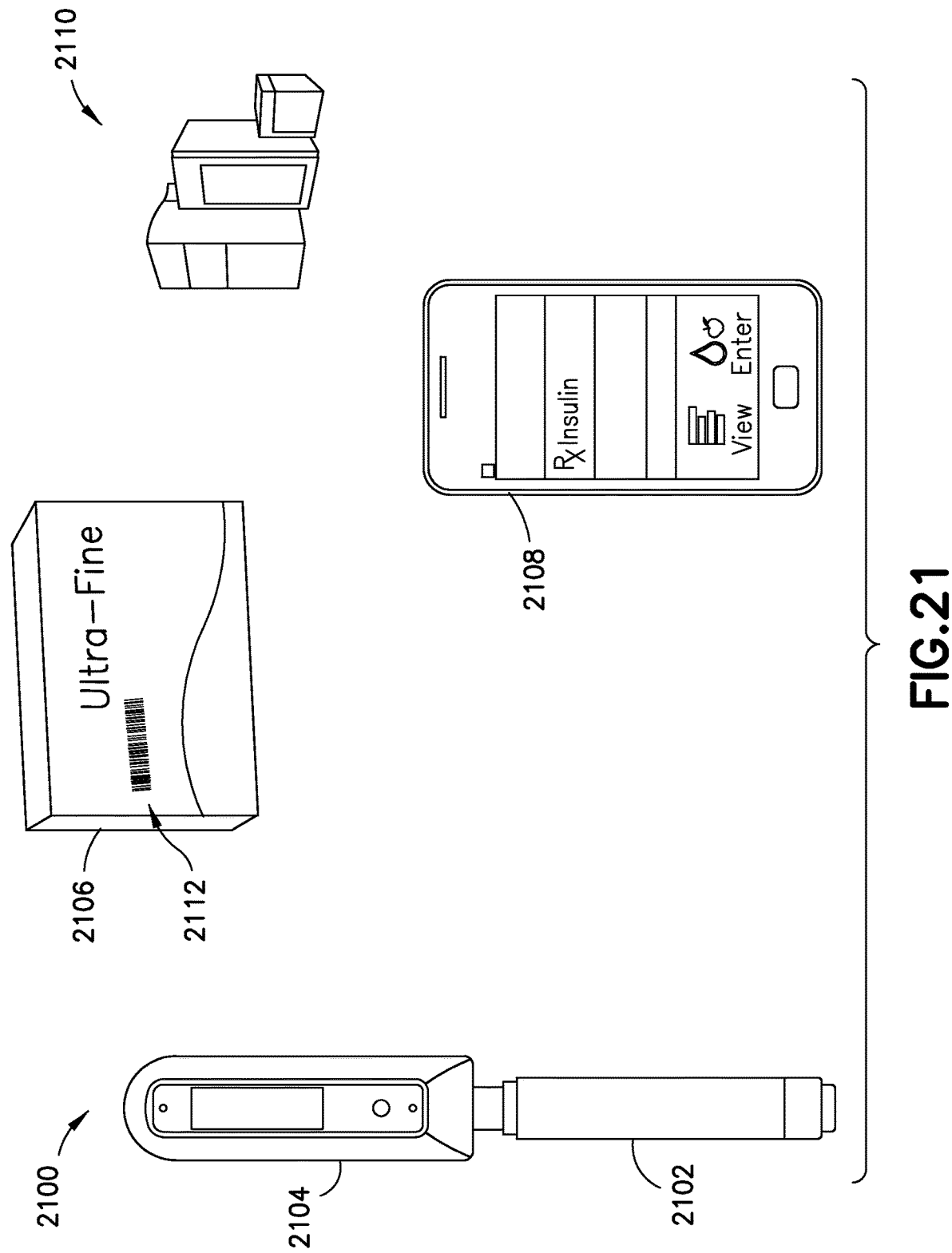
FIG. 21 illustrates a system for identifying pen needles according to an exemplary embodiment of the invention.

In addition to dose capture, informatically enabled medication delivery devices can perform additional functions. For example, an informatically enabled insulin pen with a smart cap can identify particular pen needles for use with the insulin pen. Further, the informatically enabled insulin pen can advantageously reduce or prevent unintended uses. FIG. 21 illustrates a first exemplary system 2100 including an insulin pen 2102, a smart pen cap 2104, a package of disposable pen needles 2106, and a smart phone 2108 running an application. Using the smartphone's camera, the pen needle package barcode 2112 (or any suitable identification) is read by the cellphone. The cellphone 2108 in turn communicates with a cloud-based database 2110 to verify the pen needle package by manufacturer, unit size, lot number, and other factors identified by the barcode. The cellphone 2108 could confirm the barcode validity in real time or near real time, or alternately, could periodically poll the could-based database and download a complete list of valid barcodes and associated information such that communication with the cloud-based storage is not necessary at the time the barcode is scanned. In this embodiment, the barcode 2112 is static and printed on all pen needle packages, and so is subject to reuse.

Figure 22:
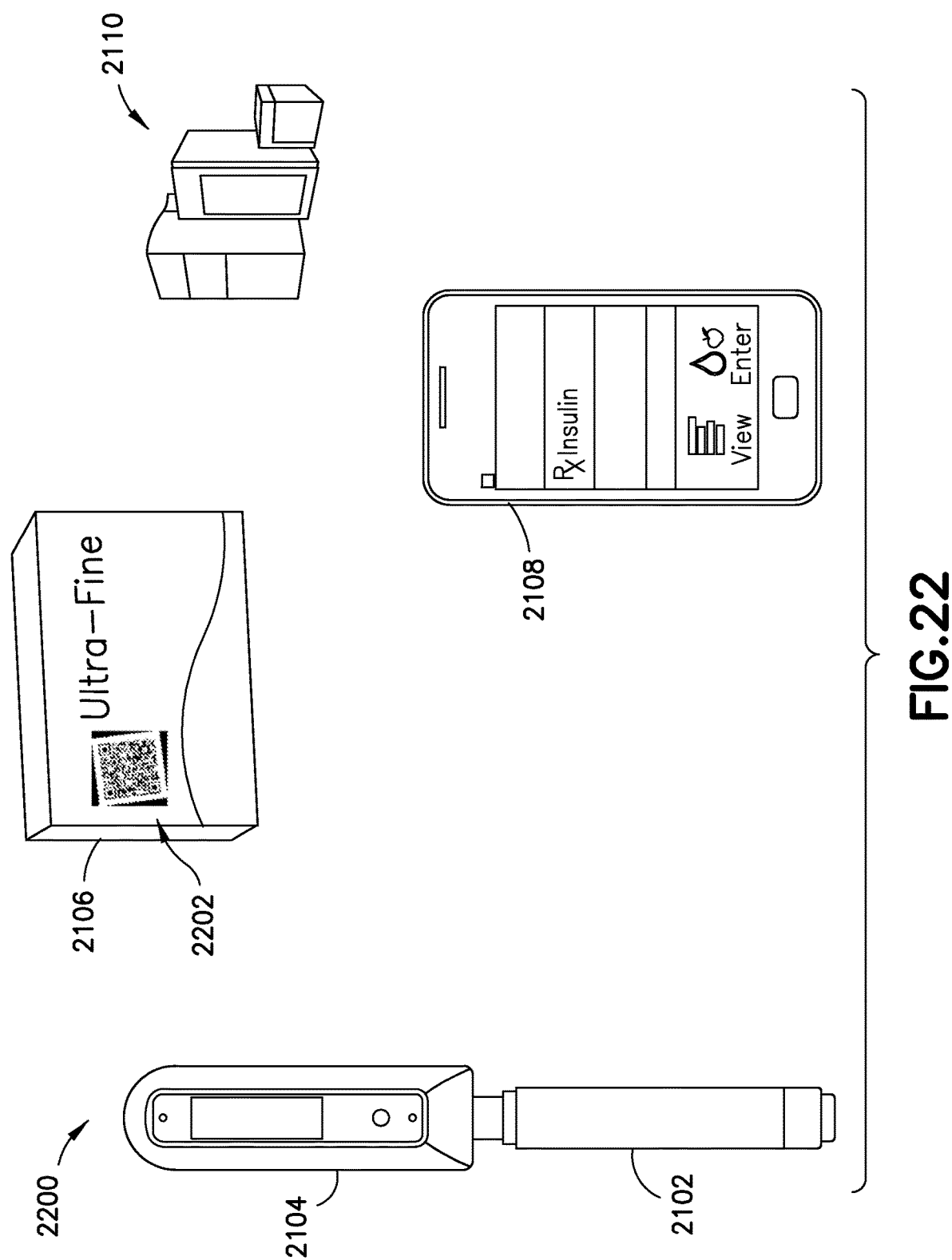
FIG. 22 illustrates another system for identifying pen needles according to an exemplary embodiment of the invention.
Figure 23:
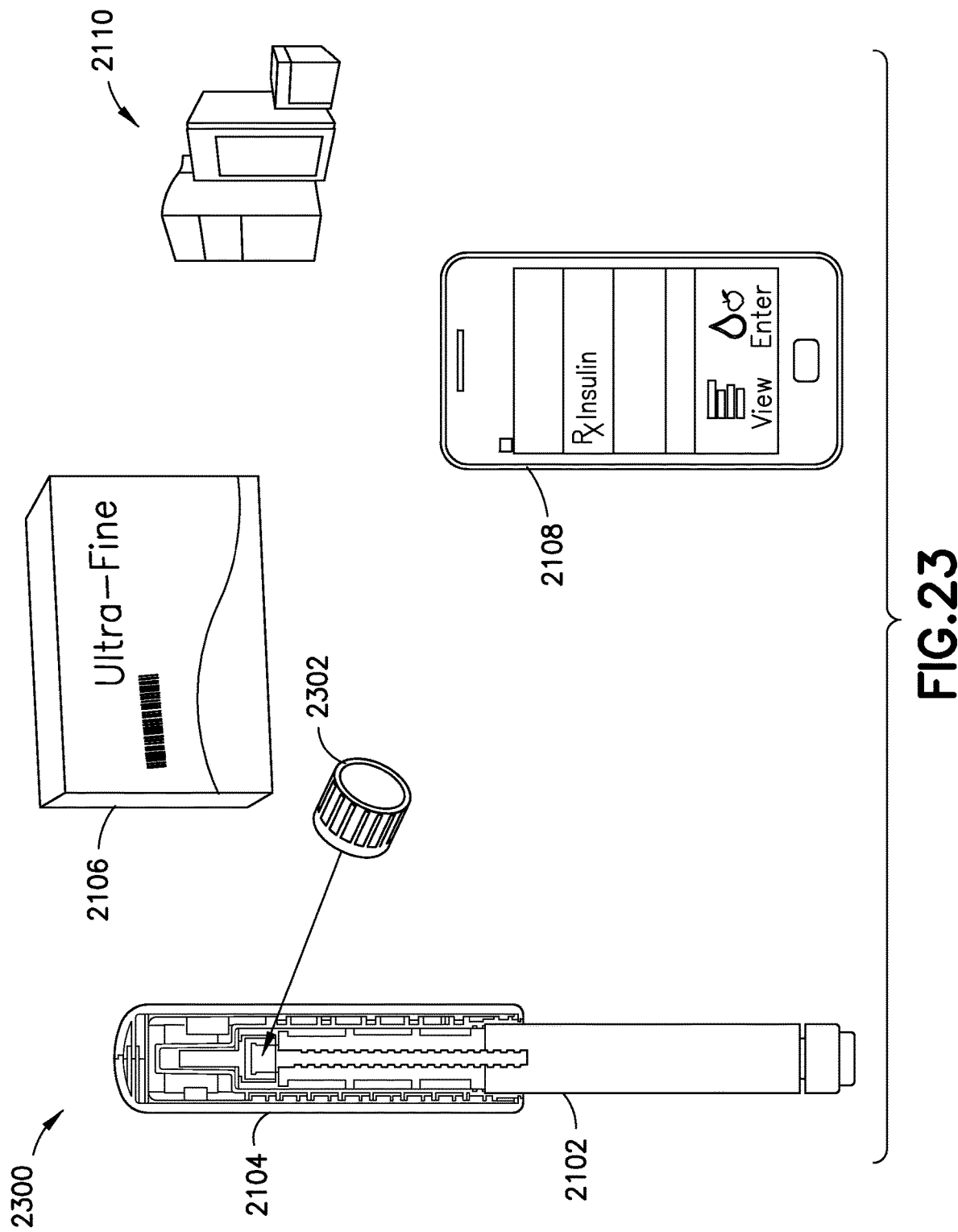
FIG. 23 illustrates another system for identifying pen needles according to an exemplary embodiment of the invention.
Figure 24:
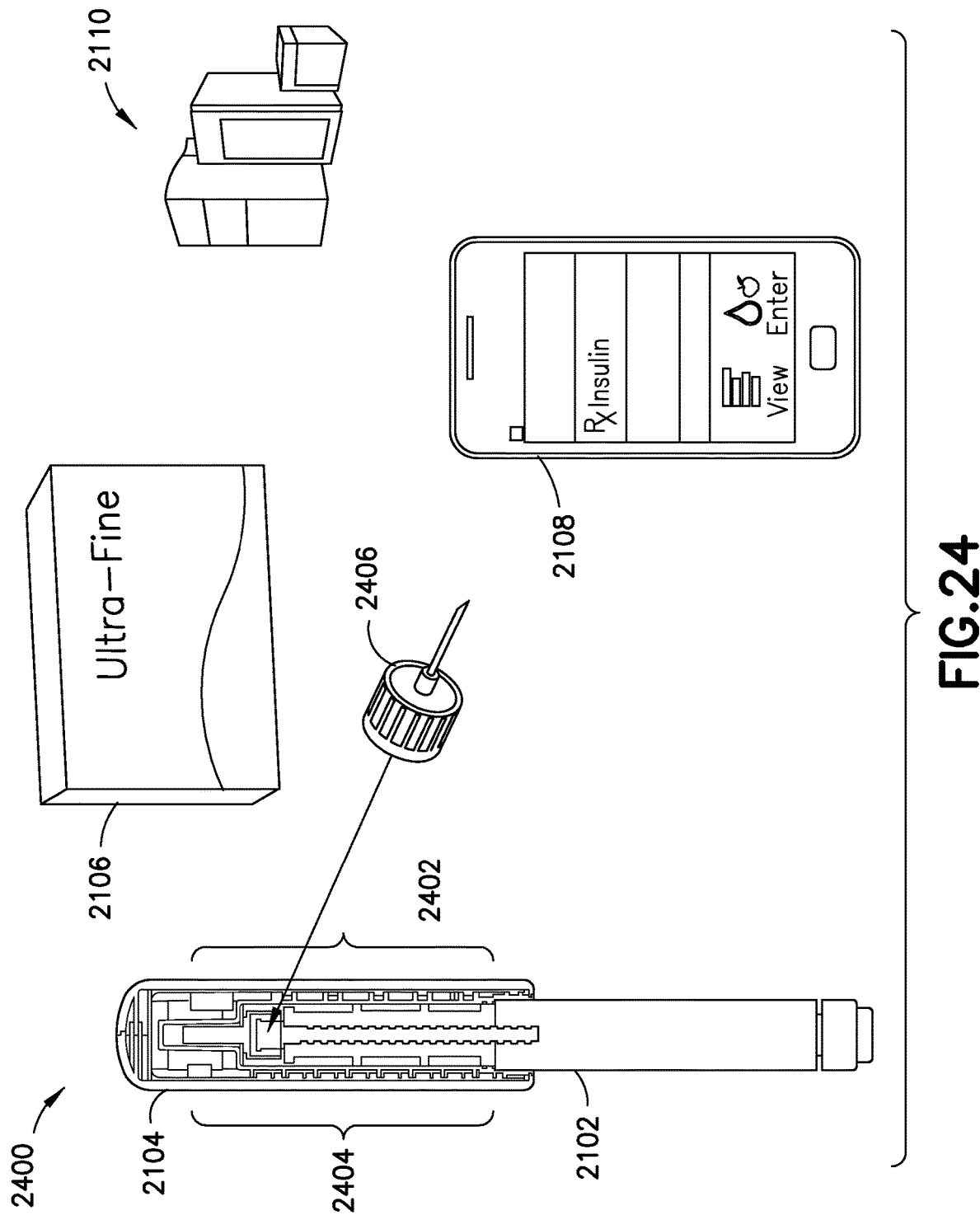
FIG. 24 illustrates yet another system for identifying pen needles according to an exemplary embodiment of the invention.

In another embodiment illustrated in FIG. 22, the system 2200 includes pen needle packages 2106 that are imprinted with unique barcodes 2202 (or any suitable unique identifier). The cellphone 2108 is used to scan the unique identifier 2202 and communicates with a cloud-based database 2110 to confirm that the unique identifier 2202 is in fact unique and remains valid. Such a system could advantageously be used to assist recalls as needed, and to prevent the use of unauthorized pen needles. In either of the exemplary systems described above, a down counter is preferably set to the number of disposable pen needles in the identified package, and certain functions are restricted after the counter reaches zero, indicating that the package should be exhausted. For example, the smart cap would stop logging delivered doses once the needle package is exhausted, and until a new package is authorized.

In another exemplary system 2300, a smart sleeve 2302 is provided in each package of disposable pen needles 2106. The smart sleeve 2302 is connected to the pen needle, and the smart sleeve contains an RFID chip. The RFID chip may be read by either the smart cap 2104, or the cellphone 2108, to verify the pen needle package. Advantageously, the smart sleeve 2302 is read by the smart cap 2104 each time the cap is placed on the insulin pen 2102. If the smart cap 2104 reads the RFID chip, the chip information is preferably transmitted to the smartphone 2108, which in turn communicates with a cloud-based database 2110 as discussed in the above described examples. RFID chips preferably include lot information, manufacturing date, and any other suitable information, and do not require printing space on the pen needle package. Similar to the example provided above, a down counter is preferably provided to restrict higher level functions once the disposable pen needles provided in the package 2106 should be exhausted. The smart sleeve 2302 preferably forms an interface between the insulin pen 2102 and pen needles using the existing threaded interfaces on the pen and pen needles. That is, the sleeve includes inward facing threads to mate with the insulin pen 2104, and outwardly facing threads to mate with the disposable pen needles. In one version the smart sleeve includes a septum and a cannula, and forms part of the flow channel between the insulin cartridge and the pen needle. In this version, the smart sleeve preferably includes a flow sensor such as a MEMS flow sensor discussed above. In another version, the pen sleeve merely contains identifying information, such as an RFID chip to identify the lot number, number of units, and other information of the disposable pen needle package. In this version the smart sleeve still includes inwardly facing and outwardly facing threads for mating with the pen and pen needles, respectively, but the sleeves forms a hollow cylinder and although the pen needles mate with the smart sleeve, the inwardly facing cannula of each pen needle still pierces the septum of the insulin pen, such that the smart sleeve does not form part of the fluid path between the insulin cartridge and the pen needle.

In another exemplary system 2400, a smart cap 2104 is provided with a bank of emitters 2402 and a bank of sensors 2404. A portion of the emitters 2402 and sensors 2404 sense the location of the plunger in the pen needle before and after an injection to verify the dose delivered to the user. At least one other emitter and sensor are located adjacent to the pen needle 2406 such that when the smart cap 2104 is attached to the pen 2102 the smart cap can identify the pen needle based on a signal received by the sensor. The smart cap 2104 communicates with the cellphone 2108, and the cellphone 2108 communicates with a cloud-based storage 2110 as discussed above. In this embodiment, proprietary disposable pen needles are advantageously marked such that the emitter and sensor recognize a unique signal identifying the pen needle as authentic. The signal may be optical, magnetic, or any other suitable signaling means.

In yet another exemplary system, all of the features above are combined. That is, the disposable pen needle package 2106 is imprinted with a unique barcode 2202 (or any suitable marking), the package of pen needles 2106 is provided with a smart sleeve 2302, and the disposable pen needles are manufactured with a unique signature, such as an optical, magnetic, or any other suitable signature signal. The smart cap 2104 triggers a down counter in the smart sleeve 2302 or the smartphone 2108, and senses the unique signature of authentic pen needles. If the pen needle is not recognized some or all functions may be restricted as discussed above. A down counter is used to restrict higher level features once the package of pen needles should be exhausted.

Although only a few embodiments of the present invention have been described, the present invention is not limited to the described embodiment. Instead, it will be appreciated by those skilled in the art that changes may be made to these embodiments without departing from the principles and spirit of the invention.

What is claimed is:

1. A device for capturing delivered dose information, comprising:
   a medication delivery device;
   a dose information capture device adapted to be attached to the medication delivery device; and
   a target element adapted to be attached to the medication delivery device;
   wherein the target element comprises a magnet, and the target element attaches to the medication delivery device on a dose delivery mechanism of the medication delivery device, the dose delivery mechanism having a full position and an empty position, and
   wherein the dose information capture device includes a single Hall-effect sensor adapted to sense a Hall-effect voltage produced by and related to proximity of the target element, the single Hall-effect sensor producing a linear output voltage that changes continuously along all positions from the full position to the empty position to detect a continuous change in absolute position of the target element corresponding to a change in position of the dose delivery mechanism before and after a plurality of single doses is delivered anywhere between said full position and said empty position;
   wherein the target element and the Hall-effect sensor are arranged to operate in a linear analog output voltage response region of the Hall-effect sensor.

2. The device of claim 1, wherein the medication delivery device comprises an RFID chip.

3. The device of claim 1, wherein the medication delivery device is a syringe and the sensor element attaches to the plunger.

4. A system for capturing delivered dose information, comprising:
   a medicament vial having a medicament volume sensor attached to a sidewall of the medicament vial;
   a processor;
   a memory comprising instructions adapted to control the processor to receive medicament volume measurements from the medicament volume sensor, and to determine a difference in volume prior to a dose delivery and after the dose delivery; and
   a plurality of magnetic beads having a density less than a density of a medicament within the medicament vial, the plurality of magnetic beads being disposed within the medicament vial and floating within the medicament in the medicament vial; and wherein the medicament volume sensor comprises a magnetic sensor in proximity to the medicament vial to detect a location of the magnetic beads within the medicament vial.

5. A system for capturing delivered dose information, comprising:
   a medicament vial having a medicament volume sensor attached to a sidewall of the medicament vial;
   a processor; and
   a memory comprising instructions adapted to control the processor to receive medicament volume measurements from the medicament volume sensor, and to determine a difference in volume prior to a dose delivery and after the dose delivery;
   wherein the medicament volume sensor comprises a capacitance sensor having capacitance as a continuous function of a medicament level within the medicament vial attached to a sidewall of the medicament vial;

wherein a number of the plurality of magnetic beads is sufficient to substantially cover an exposed surface of the medicament within the vial.

\* \* \* \* \*